US011633206B2

(12) United States Patent
Deepa

(10) Patent No.: US 11,633,206 B2
(45) Date of Patent: Apr. 25, 2023

(54) CATHETER WITH RETRACTABLE SHEATH AND METHODS THEREOF

(71) Applicant: C. R. Bard, Inc., Franklin Lakes, NJ (US)

(72) Inventor: Deepa Deepa, Gilbert, AZ (US)

(73) Assignee: C.R. Bard, Inc., Franklin Lakes, NJ (US)

(*) Notice: Subject to any disclaimer, the term of this patent is extended or adjusted under 35 U.S.C. 154(b) by 1010 days.

(21) Appl. No.: 16/462,260

(22) PCT Filed: Nov. 6, 2017

(86) PCT No.: PCT/US2017/060195
§ 371 (c)(1),
(2) Date: May 20, 2019

(87) PCT Pub. No.: WO2018/097953
PCT Pub. Date: May 31, 2018

(65) Prior Publication Data
US 2019/0365408 A1 Dec. 5, 2019

Related U.S. Application Data

(63) Continuation of application No. 15/360,834, filed on Nov. 23, 2016, now abandoned.

(51) Int. Cl.
A61B 17/32 (2006.01)
A61B 17/22 (2006.01)
A61B 17/00 (2006.01)

(52) U.S. Cl.
CPC ............... A61B 17/320068 (2013.01); A61B 17/22012 (2013.01); A61B 2017/00973 (2013.01);
(Continued)

(58) Field of Classification Search
CPC ........ A61B 17/22004; A61B 17/22012; A61B 17/22014; A61B 17/320068; A61B 17/320092; A61B 2017/320069
See application file for complete search history.

(56) References Cited

U.S. PATENT DOCUMENTS 3,296,620 A 1/1967 Rodda
3,433,226 A 3/1969 Boyd
(Continued)

FOREIGN PATENT DOCUMENTS

AU 2007240154 A1 1/2008
DE 2256127 A1 5/1974
(Continued)

OTHER PUBLICATIONS

Calhoun et al., "Electron-Beam Systems for Medical Device Sterilization", downloaded from web on Oct. 8, 2002 <http://www.devicelink.com/mpb/archive/97/07/002.html> 7 pages total.
(Continued)

Primary Examiner — Todd J Scherbel
(74) Attorney, Agent, or Firm — Dinsmore & Shohl LLP

(57) ABSTRACT

A method for using an endoluminal device to modify an intravascular lesion includes providing an ultrasound-producing mechanism that converts an electric current into vibrational energy at an ultrasonic frequency; providing a sheath including a sheath lumen, wherein the sheath is configured to retract from a first, fully extended position of the sheath and extend from a second, fully retracted position of the sheath; providing a core wire disposed within the sheath lumen of the sheath, the core wire being coupled to the ultrasound-producing mechanism via a sonic connector, the core wire being excited by the vibrational energy at the ultrasonic frequency when the ultrasound-producing mechanism is activated; and retracting the sheath relative to the core wire to expose a working length of a distal portion of (Continued)

Figure 1:
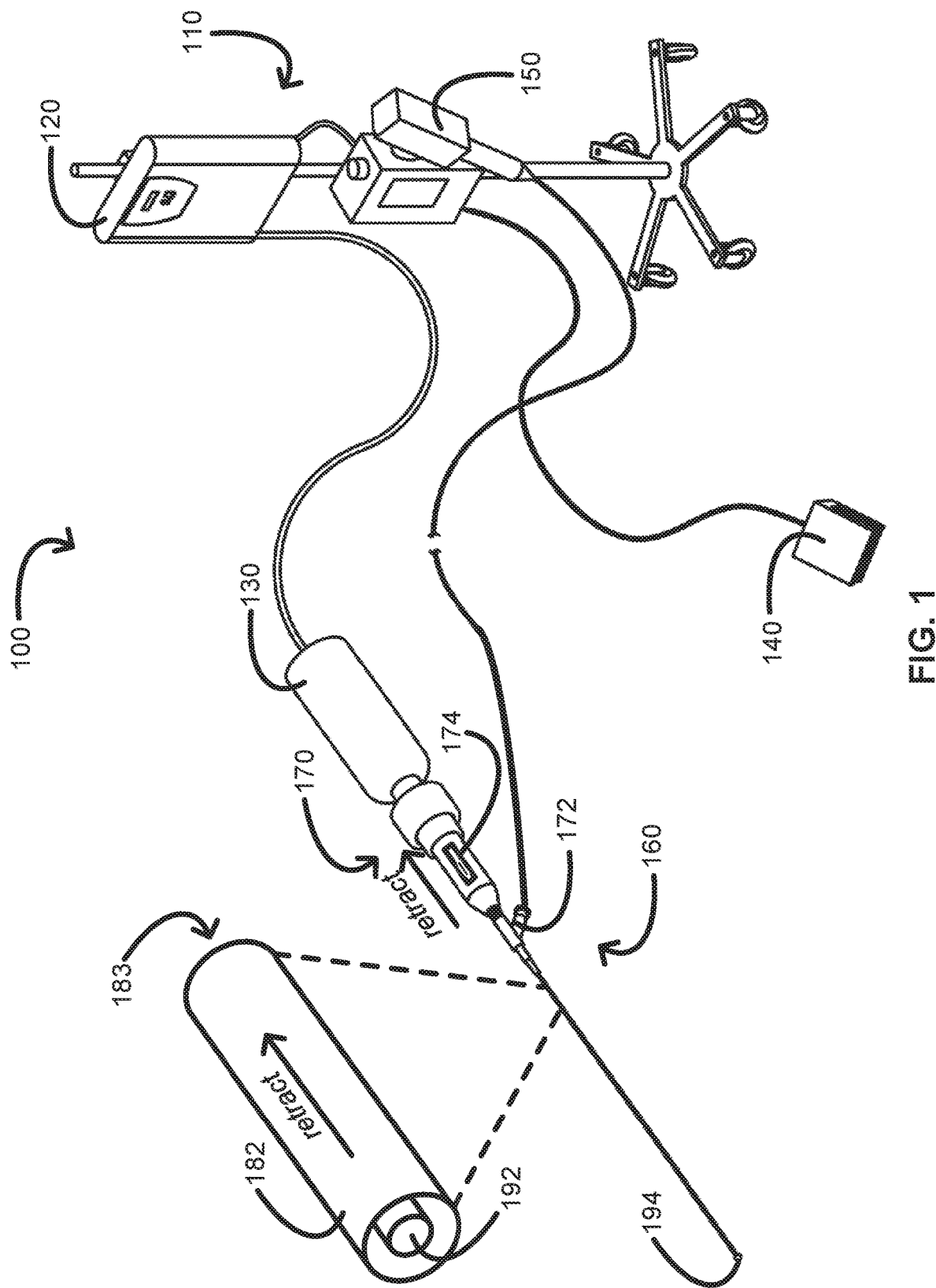

the core wire for ultrasound-based modification of one or more intravascular lesions.

14 Claims, 10 Drawing Sheets

(52) U.S. Cl.
CPC .............. *A61B 2017/22014* (2013.01); *A61B 2017/22075* (2013.01); *A61B 2017/320069* (2017.08); *A61B 2017/320072* (2013.01)

(56) References Cited

U.S. PATENT DOCUMENTS

| | | | |
|---|---|---|---|
| 3,443,226 A | 5/1969 | Knight |
| 3,565,062 A | 2/1971 | Kurls |
| 3,585,082 A | 6/1971 | Siller |
| 3,612,038 A | 10/1971 | Halligan |
| 3,631,848 A | 1/1972 | Muller |
| 3,679,378 A | 7/1972 | Van Impe et al. |
| 3,719,737 A | 3/1973 | Vaillancourt et al. |
| 3,739,460 A | 6/1973 | Addis et al. |
| 3,754,746 A | 8/1973 | Thiele |
| 3,823,717 A | 7/1974 | Pohlman et al. |
| 3,835,690 A | 9/1974 | Leonhardt et al. |
| 3,839,841 A | 10/1974 | Amplatz |
| 3,896,811 A | 7/1975 | Storz |
| 4,016,882 A | 4/1977 | Broadwin et al. |
| 4,033,331 A | 7/1977 | Guss et al. |
| 4,136,700 A | 1/1979 | Broadwin et al. |
| 4,337,090 A | 6/1982 | Harrison |
| 4,368,410 A | 1/1983 | Hance et al. |
| 4,417,578 A | 11/1983 | Banko |
| 4,425,115 A | 1/1984 | Wuchinich |
| 4,449,523 A | 5/1984 | Szachowicz et al. |
| 4,453,935 A | 6/1984 | Newton |
| 4,486,680 A | 12/1984 | Bonnet et al. |
| 4,505,767 A | 3/1985 | Quin |
| 4,535,759 A | 8/1985 | Polk et al. |
| 4,545,767 A | 10/1985 | Suzuki et al. |
| 4,565,589 A | 1/1986 | Harrison |
| 4,565,787 A | 1/1986 | Bossle et al. |
| 4,572,184 A | 2/1986 | Stohl et al. |
| 4,664,112 A | 5/1987 | Kensey et al. |
| 4,665,906 A | 5/1987 | Jervis |
| 4,679,558 A | 7/1987 | Kensey et al. |
| 4,700,705 A | 10/1987 | Kensey et al. |
| 4,721,117 A | 1/1988 | Mar et al. |
| 4,750,902 A | 6/1988 | Wuchinich et al. |
| 4,781,186 A | 11/1988 | Simpson et al. |
| 4,808,153 A | 2/1989 | Parisi |
| 4,811,743 A | 3/1989 | Stevens |
| 4,827,911 A | 5/1989 | Broadwin et al. |
| 4,838,853 A | 6/1989 | Parisi |
| 4,854,325 A | 8/1989 | Stevens |
| 4,870,953 A | 10/1989 | DonMicheal et al. |
| 4,886,060 A | 12/1989 | Wiksell |
| 4,920,954 A | 5/1990 | Alliger et al. |
| 4,923,462 A | 5/1990 | Stevens |
| 4,924,863 A | 5/1990 | Sterzer |
| 4,931,047 A | 6/1990 | Broadwin et al. |
| 4,936,281 A | 6/1990 | Stasz |
| 4,936,845 A | 6/1990 | Stevens |
| 4,979,952 A | 12/1990 | Kubota et al. |
| 5,000,185 A | 3/1991 | Yock |
| 5,015,227 A | 5/1991 | Broadwin et al. |
| 5,026,384 A | 6/1991 | Farr et al. |
| 5,030,201 A | 7/1991 | Palestrant |
| 5,030,357 A | 7/1991 | Lowe |
| 5,046,503 A | 9/1991 | Schneiderman |
| 5,053,008 A | 10/1991 | Bajaj |
| 5,058,570 A | 10/1991 | Idemoto et al. |
| 5,076,276 A | 12/1991 | Sakurai et al. |
| 5,091,205 A | 2/1992 | Fan |
| 5,100,423 A | 3/1992 | Fearnot |
| 5,109,859 A | 5/1992 | Jenkins |
| 5,114,414 A | 5/1992 | Buchbinder |
| 5,116,350 A | 5/1992 | Stevens |
| 5,127,917 A | 7/1992 | Niederhauser et al. |
| 5,131,393 A | 7/1992 | Ishiguro et al. |
| 5,156,143 A | 10/1992 | Bocquet et al. |
| 5,163,421 A | 11/1992 | Bernstein et al. |
| 5,171,216 A | 12/1992 | Dasse et al. |
| 5,180,363 A | 1/1993 | Idemoto et al. |
| 5,183,470 A | 2/1993 | Wettermann |
| 5,195,955 A | 3/1993 | Don Michael |
| 5,215,614 A | 6/1993 | Wijkamp et al. |
| 5,217,565 A | 6/1993 | Kou et al. |
| 5,221,255 A | 6/1993 | Mahurkar et al. |
| 5,226,421 A | 7/1993 | Frisbie et al. |
| 5,234,416 A | 8/1993 | Macaulay et al. |
| 5,236,414 A | 8/1993 | Takasu |
| 5,238,004 A | 8/1993 | Sahatjian et al. |
| 5,242,385 A | 9/1993 | Strukel |
| 5,243,997 A | 9/1993 | Uflacker et al. |
| 5,248,296 A | 9/1993 | Alliger |
| 5,255,669 A | 10/1993 | Kubota et al. |
| 5,267,954 A | 12/1993 | Nita |
| 5,269,291 A | 12/1993 | Carter |
| 5,269,297 A | 12/1993 | Weng et al. |
| 5,269,793 A | 12/1993 | Simpson |
| 5,279,546 A | 1/1994 | Mische et al. |
| 5,287,858 A | 2/1994 | Hammerslag et al. |
| 5,290,229 A | 3/1994 | Paskar |
| 5,304,115 A | 4/1994 | Pflueger et al. |
| 5,304,131 A | 4/1994 | Paskar |
| 5,312,328 A | 5/1994 | Nita et al. |
| 5,318,014 A | 6/1994 | Carter |
| 5,318,570 A | 6/1994 | Hood et al. |
| 5,324,255 A | 6/1994 | Passafaro et al. |
| 5,324,260 A | 6/1994 | O'Neill et al. |
| 5,325,860 A | 7/1994 | Seward et al. |
| 5,326,342 A | 7/1994 | Pflueger et al. |
| 5,328,004 A | 7/1994 | Fannin et al. |
| 5,329,927 A | 7/1994 | Gardineer et al. |
| 5,341,818 A | 8/1994 | Abrams et al. |
| 5,342,292 A | 8/1994 | Nita et al. |
| 5,344,395 A | 9/1994 | Whalen et al. |
| 5,346,502 A | 9/1994 | Estabrook et al. |
| 5,362,309 A | 11/1994 | Carter |
| 5,368,557 A | 11/1994 | Nita |
| 5,368,558 A | 11/1994 | Nita et al. |
| 5,376,084 A | 12/1994 | Bacich et al. |
| 5,378,234 A | 1/1995 | Hammerslag et al. |
| 5,380,274 A | 1/1995 | Nita |
| 5,380,316 A | 1/1995 | Aita et al. |
| 5,382,228 A | 1/1995 | Nita et al. |
| 5,383,460 A | 1/1995 | Jang et al. |
| 5,389,096 A | 2/1995 | Aita et al. |
| 5,391,144 A | 2/1995 | Sakurai et al. |
| 5,397,293 A | 3/1995 | Alliger et al. |
| 5,397,301 A | 3/1995 | Pflueger et al. |
| 5,403,324 A | 4/1995 | Ciervo et al. |
| 5,405,318 A | 4/1995 | Nita |
| 5,409,483 A | 4/1995 | Campbell et al. |
| 5,417,672 A | 5/1995 | Nita et al. |
| 5,417,703 A | 5/1995 | Brown et al. |
| 5,421,923 A | 6/1995 | Clarke et al. |
| 5,427,118 A | 6/1995 | Nita et al. |
| 5,431,168 A | 7/1995 | Webster, Jr. |
| 5,431,663 A | 7/1995 | Carter |
| 5,443,078 A | 8/1995 | Uflacker |
| 5,447,509 A | 9/1995 | Mills et al. |
| 5,449,369 A | 9/1995 | Imran |
| 5,449,370 A | 9/1995 | Vaitekunas |
| 5,451,209 A | 9/1995 | Ainsworth et al. |
| 5,462,529 A | 10/1995 | Simpson et al. |
| 5,465,733 A | 11/1995 | Hinohara et al. |
| 5,474,530 A | 12/1995 | Passafaro et al. |
| 5,474,531 A | 12/1995 | Carter |
| 5,480,379 A | 1/1996 | La Rosa |
| 5,484,398 A | 1/1996 | Stoddard |
| 5,487,757 A | 1/1996 | Truckai et al. |
| 5,498,236 A | 3/1996 | Dubrul et al. |

(56) References Cited

U.S. PATENT DOCUMENTS

| | | |
|---|---|---|
| 5,507,738 A | 4/1996 | Ciervo |
| 5,516,043 A | 5/1996 | Manna et al. |
| 5,527,273 A | 6/1996 | Manna et al. |
| 5,538,512 A | 7/1996 | Zenzon et al. |
| 5,540,656 A | 7/1996 | Pflueger et al. |
| 5,542,917 A | 8/1996 | Nita et al. |
| 5,597,497 A | 1/1997 | Dean et al. |
| 5,597,882 A | 1/1997 | Schiller et al. |
| 5,607,421 A | 3/1997 | Jeevanandam et al. |
| 5,611,807 A | 3/1997 | O'Boyle |
| 5,618,266 A | 4/1997 | Liprie |
| 5,626,593 A | 5/1997 | Imran |
| 5,627,365 A | 5/1997 | Chiba et al. |
| 5,649,935 A | 7/1997 | Kremer et al. |
| 5,658,282 A | 8/1997 | Daw et al. |
| 5,665,062 A | 9/1997 | Houser |
| 5,685,841 A | 11/1997 | Mackool |
| 5,695,460 A | 12/1997 | Siegel et al. |
| 5,695,507 A | 12/1997 | Auth et al. |
| 5,715,825 A | 2/1998 | Crowley |
| 5,720,724 A | 2/1998 | Ressemann et al. |
| 5,725,494 A | 3/1998 | Brisken |
| 5,728,062 A | 3/1998 | Brisken |
| 5,738,100 A | 4/1998 | Yagami et al. |
| 5,797,876 A | 8/1998 | Spears et al. |
| 5,816,923 A | 10/1998 | Milo et al. |
| 5,827,203 A | 10/1998 | Nita |
| 5,827,971 A | 10/1998 | Hale et al. |
| 5,830,127 A | 11/1998 | DeCastro |
| 5,830,222 A | 11/1998 | Makower |
| 5,846,218 A | 12/1998 | Brisken et al. |
| 5,873,835 A | 2/1999 | Hastings et al. |
| 5,876,385 A | 3/1999 | Ikari et al. |
| 5,893,838 A | 4/1999 | Daoud et al. |
| 5,895,397 A | 4/1999 | Jang et al. |
| 5,902,287 A | 5/1999 | Martin |
| 5,904,667 A | 5/1999 | Falwell |
| 5,916,192 A | 6/1999 | Nita et al. |
| 5,916,912 A | 6/1999 | Ames et al. |
| 5,935,142 A | 8/1999 | Hood |
| 5,935,144 A | 8/1999 | Estabrook |
| 5,937,301 A | 8/1999 | Gardner et al. |
| 5,944,737 A | 8/1999 | Tsonton et al. |
| 5,957,882 A | 9/1999 | Nita et al. |
| 5,957,899 A | 9/1999 | Spears et al. |
| 5,964,223 A | 10/1999 | Baran |
| 5,967,984 A | 10/1999 | Chu et al. |
| 5,971,949 A | 10/1999 | Levin et al. |
| 5,976,119 A | 11/1999 | Spears et al. |
| 5,989,208 A | 11/1999 | Nita |
| 5,989,275 A | 11/1999 | Estabrook et al. |
| 5,997,497 A | 12/1999 | Nita et al. |
| 6,004,280 A | 12/1999 | Buck et al. |
| 6,004,335 A | 12/1999 | Vaitekunas et al. |
| 6,007,499 A | 12/1999 | Martin et al. |
| 6,007,514 A | 12/1999 | Nita |
| 6,022,309 A | 2/2000 | Celliers et al. |
| 6,024,764 A | 2/2000 | Schroeppel |
| 6,029,671 A | 2/2000 | Stevens et al. |
| 6,030,357 A | 2/2000 | Daoud et al. |
| 6,036,689 A | 3/2000 | Tu et al. |
| 6,051,010 A | 4/2000 | DiMatteo et al. |
| 6,066,135 A | 5/2000 | Honda |
| 6,113,558 A | 9/2000 | Rosenschein et al. |
| 6,120,515 A | 9/2000 | Rogers et al. |
| 6,123,698 A | 9/2000 | Spears et al. |
| 6,142,971 A | 11/2000 | Daoud et al. |
| 6,149,596 A | 11/2000 | Bancroft |
| 6,159,176 A | 12/2000 | Broadwin et al. |
| 6,159,187 A | 12/2000 | Park et al. |
| 6,165,127 A | 12/2000 | Crowley |
| 6,165,188 A | 12/2000 | Saadat et al. |
| 6,179,809 B1 | 1/2001 | Khairkhahan et al. |
| 6,180,059 B1 | 1/2001 | Divino, Jr. et al. |
| 6,190,353 B1 | 2/2001 | Makower et al. |
| 6,206,842 B1 | 3/2001 | Tu et al. |
| 6,210,356 B1 | 4/2001 | Anderson et al. |
| 6,217,543 B1 | 4/2001 | Anis et al. |
| 6,217,565 B1 | 4/2001 | Cohen |
| 6,217,588 B1 | 4/2001 | Jerger et al. |
| 6,221,015 B1 | 4/2001 | Yock |
| 6,231,546 B1 | 5/2001 | Milo et al. |
| 6,231,587 B1 | 5/2001 | Makower |
| 6,235,007 B1 | 5/2001 | Divino, Jr. et al. |
| 6,241,692 B1 | 6/2001 | Tu et al. |
| 6,241,703 B1 | 6/2001 | Levin et al. |
| 6,241,744 B1 | 6/2001 | Imran et al. |
| 6,248,087 B1 | 6/2001 | Spears et al. |
| 6,277,084 B1 | 8/2001 | Abele et al. |
| 6,283,983 B1 | 9/2001 | Makower et al. |
| 6,287,271 B1 | 9/2001 | Dubrul et al. |
| 6,287,285 B1 | 9/2001 | Michal et al. |
| 6,287,317 B1 | 9/2001 | Makower et al. |
| 6,296,620 B1 | 10/2001 | Gesswein et al. |
| 6,298,620 B1 | 10/2001 | Hatzinikolas |
| 6,302,875 B1 | 10/2001 | Makower et al. |
| 6,309,358 B1 | 10/2001 | Okubo |
| 6,315,741 B1 | 11/2001 | Martin et al. |
| 6,315,754 B1 | 11/2001 | Daoud et al. |
| 6,331,171 B1 | 12/2001 | Cohen |
| 6,346,192 B2 | 2/2002 | Buhr et al. |
| 6,379,378 B1 | 4/2002 | Werneth et al. |
| 6,387,109 B1 | 5/2002 | Davison et al. |
| 6,387,324 B1 | 5/2002 | Patterson et al. |
| 6,394,956 B1 | 5/2002 | Chandrasekaran et al. |
| 6,398,736 B1 | 6/2002 | Seward |
| 6,409,673 B2 | 6/2002 | Yock |
| 6,416,533 B1 | 7/2002 | Gobin et al. |
| 6,423,026 B1 | 7/2002 | Gesswein et al. |
| 6,427,118 B1 | 7/2002 | Suzuki |
| 6,433,464 B2 | 8/2002 | Jones |
| 6,434,418 B1 | 8/2002 | Neal et al. |
| 6,450,975 B1 | 9/2002 | Brennan et al. |
| 6,454,737 B1 | 9/2002 | Nita et al. |
| 6,454,757 B1 | 9/2002 | Nita et al. |
| 6,454,997 B1 | 9/2002 | Divino, Jr. et al. |
| 6,484,052 B1 | 11/2002 | Visuri et al. |
| 6,491,707 B2 | 12/2002 | Makower et al. |
| 6,494,891 B1 | 12/2002 | Cornish et al. |
| 6,494,894 B2 | 12/2002 | Mirarchi |
| 6,500,141 B1 | 12/2002 | Irion et al. |
| 6,508,781 B1 | 1/2003 | Brennan et al. |
| 6,508,784 B1 | 1/2003 | Shu |
| 6,511,458 B2 | 1/2003 | Milo et al. |
| 6,514,249 B1 | 2/2003 | Maguire et al. |
| 6,524,251 B2 | 2/2003 | Rabiner et al. |
| 6,533,766 B1 | 3/2003 | Patterson et al. |
| 6,544,215 B1 | 4/2003 | Bencini et al. |
| 6,547,754 B1 | 4/2003 | Evans et al. |
| 6,547,788 B1 | 4/2003 | Maguire et al. |
| 6,551,337 B1 | 4/2003 | Rabiner et al. |
| 6,554,846 B2 | 4/2003 | Hamilton et al. |
| 6,555,059 B1 | 4/2003 | Myrick et al. |
| 6,558,502 B2 | 5/2003 | Divino, Jr. et al. |
| 6,562,031 B2 | 5/2003 | Chandrasekaran et al. |
| 6,573,470 B1 | 6/2003 | Brown et al. |
| 6,576,807 B1 | 6/2003 | Brunelot et al. |
| 6,582,387 B2 | 6/2003 | Derek et al. |
| 6,589,253 B1 | 7/2003 | Cornish et al. |
| 6,595,989 B1 | 7/2003 | Schaer |
| 6,596,235 B2 | 7/2003 | Divino, Jr. et al. |
| 6,602,467 B1 | 8/2003 | Divino, Jr. et al. |
| 6,602,468 B2 | 8/2003 | Patterson et al. |
| 6,605,217 B2 | 8/2003 | Buhr et al. |
| 6,607,698 B1 | 8/2003 | Spears et al. |
| 6,610,077 B1 | 8/2003 | Hancock et al. |
| 6,613,280 B2 | 9/2003 | Myrick et al. |
| 6,615,062 B2 | 9/2003 | Ryan et al. |
| 6,616,617 B1 | 9/2003 | Ferrera et al. |
| 6,622,542 B2 | 9/2003 | Derek et al. |
| 6,623,448 B2 | 9/2003 | Slater |
| 6,635,017 B1 | 10/2003 | Moehring et al. |
| 6,650,923 B1 | 11/2003 | Lesh et al. |
| 6,652,547 B2 | 11/2003 | Rabiner et al. |

(56) References Cited

U.S. PATENT DOCUMENTS

| | | |
|---|---|---|
| 6,660,013 B2 | 12/2003 | Rabiner et al. |
| 6,676,900 B1 | 1/2004 | Divino, Jr. et al. |
| 6,682,502 B2 | 1/2004 | Bond et al. |
| 6,685,657 B2 | 2/2004 | Jones |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,810 B2 | 2/2004 | Peacock, III et al. |
| 6,702,748 B1 | 3/2004 | Nita et al. |
| 6,702,750 B2 | 3/2004 | Yock |
| 6,719,715 B2 | 4/2004 | Newman et al. |
| 6,719,725 B2 | 4/2004 | Milo et al. |
| 6,729,334 B1 | 5/2004 | Baran |
| 6,733,451 B2 | 5/2004 | Rabiner et al. |
| 6,758,846 B2 | 7/2004 | Goble et al. |
| 6,761,698 B2 | 7/2004 | Shibata et al. |
| 6,768,433 B1 | 7/2004 | Toth et al. |
| 6,814,727 B2 | 11/2004 | Mansouri-Ruiz |
| 6,855,123 B2 | 2/2005 | Nita |
| 6,866,670 B2 | 3/2005 | Rabiner et al. |
| 6,936,025 B1 | 8/2005 | Evans et al. |
| 6,936,056 B2 | 8/2005 | Nash et al. |
| 6,942,620 B2 | 9/2005 | Nita et al. |
| 6,942,677 B2 | 9/2005 | Nita et al. |
| 6,955,680 B2 | 10/2005 | Satou et al. |
| 7,004,173 B2 | 2/2006 | Sparks et al. |
| 7,004,176 B2 | 2/2006 | Lau |
| 7,056,294 B2 | 6/2006 | Khairkhahan et al. |
| 7,131,983 B2 | 11/2006 | Murakami |
| 7,137,963 B2 | 11/2006 | Nita et al. |
| 7,149,587 B2 | 12/2006 | Wardle et al. |
| 7,150,853 B2 | 12/2006 | Lee et al. |
| 7,166,098 B1 | 1/2007 | Steward et al. |
| 7,220,233 B2 | 5/2007 | Nita et al. |
| 7,267,650 B2 | 9/2007 | Chow et al. |
| 7,297,131 B2 | 11/2007 | Nita |
| 7,335,180 B2 | 2/2008 | Nita et al. |
| 7,341,569 B2 | 3/2008 | Soltani et al. |
| 7,384,407 B2 | 6/2008 | Rodriguez et al. |
| 7,393,338 B2 | 7/2008 | Nita |
| 7,421,900 B2 | 9/2008 | Karasawa et al. |
| 7,425,198 B2 | 9/2008 | Moehring et al. |
| 7,494,468 B2 | 2/2009 | Rabiner et al. |
| 7,503,895 B2 | 3/2009 | Rabiner et al. |
| 7,540,852 B2 | 6/2009 | Nita et al. |
| 7,604,608 B2 | 10/2009 | Nita et al. |
| 7,621,902 B2 | 11/2009 | Nita et al. |
| 7,621,929 B2 | 11/2009 | Nita et al. |
| 7,628,763 B2 | 12/2009 | Noriega et al. |
| 7,648,478 B2 | 1/2010 | Soltani et al. |
| 7,758,510 B2 | 7/2010 | Nita et al. |
| 7,771,358 B2 | 8/2010 | Moehring et al. |
| 7,771,452 B2 | 8/2010 | Pal et al. |
| 7,775,994 B2 | 8/2010 | Lockhart |
| 7,776,025 B2 | 8/2010 | Bobo, Jr. |
| 7,819,013 B2 | 10/2010 | Chan et al. |
| 7,850,623 B2 | 12/2010 | Griffin et al. |
| 7,918,819 B2 | 4/2011 | Karmarkar et al. |
| 7,935,108 B2 | 5/2011 | Baxter et al. |
| 7,938,819 B2 | 5/2011 | Kugler et al. |
| 7,942,809 B2 | 5/2011 | Leban |
| 7,955,293 B2 | 6/2011 | Nita et al. |
| 7,993,308 B2 | 8/2011 | Rule et al. |
| 8,038,693 B2 | 10/2011 | Allen |
| 8,043,251 B2 | 10/2011 | Nita et al. |
| 8,052,607 B2 | 11/2011 | Byrd |
| 8,083,727 B2 | 12/2011 | Kugler et al. |
| 8,133,236 B2 | 3/2012 | Nita |
| 8,152,753 B2 | 4/2012 | Nita et al. |
| 8,172,758 B2 | 5/2012 | Harhen |
| 8,221,343 B2 | 7/2012 | Nita et al. |
| 8,226,566 B2 | 7/2012 | Nita |
| 8,246,643 B2 | 8/2012 | Nita |
| 8,257,378 B1 | 9/2012 | O'Connor |
| 8,308,677 B2 | 11/2012 | Nita et al. |
| 8,343,134 B2 | 1/2013 | Kost et al. |
| 8,414,543 B2 * | 4/2013 | McGuckin, Jr. .............. A61B 17/320758 604/247 |
| 8,496,669 B2 | 7/2013 | Nita et al. |
| 8,506,519 B2 | 8/2013 | Nita |
| 8,613,700 B2 | 12/2013 | Ueno et al. |
| 8,613,751 B2 | 12/2013 | Nita et al. |
| 8,617,096 B2 | 12/2013 | Nita et al. |
| 8,632,560 B2 | 1/2014 | Pal et al. |
| 8,641,630 B2 | 2/2014 | Nita et al. |
| 8,647,293 B2 | 2/2014 | Nita |
| 8,647,296 B2 | 2/2014 | Moberg et al. |
| 8,663,259 B2 | 3/2014 | Levine et al. |
| 8,668,709 B2 | 3/2014 | Nita et al. |
| 8,690,818 B2 | 4/2014 | Bennett et al. |
| 8,690,819 B2 | 4/2014 | Nita et al. |
| 8,702,595 B2 | 4/2014 | Ueki |
| 8,708,892 B2 | 4/2014 | Sugiyama et al. |
| 8,708,994 B2 | 4/2014 | Pettis et al. |
| 8,725,228 B2 | 5/2014 | Koblish et al. |
| 8,764,700 B2 | 7/2014 | Zhang et al. |
| 8,790,291 B2 | 7/2014 | Nita et al. |
| 8,974,446 B2 | 3/2015 | Nguyen et al. |
| 8,978,478 B2 | 3/2015 | Ishioka |
| 9,101,387 B2 | 8/2015 | Plowe et al. |
| 9,107,590 B2 | 8/2015 | Hansmann et al. |
| 9,237,837 B2 | 1/2016 | Omoto et al. |
| 9,265,520 B2 | 2/2016 | Nita |
| 9,282,984 B2 | 3/2016 | Nita |
| 9,314,258 B2 | 4/2016 | Nita et al. |
| 9,381,027 B2 | 7/2016 | Nita et al. |
| 9,421,024 B2 | 8/2016 | Nita et al. |
| 9,433,433 B2 | 9/2016 | Nita et al. |
| 9,603,615 B2 | 3/2017 | Sarge |
| 9,770,250 B2 | 9/2017 | Nita et al. |
| 9,955,994 B2 | 5/2018 | Nita |
| 10,004,520 B2 | 6/2018 | Nita et al. |
| 10,130,380 B2 | 11/2018 | Nita et al. |
| 2002/0022858 A1 | 2/2002 | Demond et al. |
| 2002/0049409 A1 | 4/2002 | Noda et al. |
| 2002/0077550 A1 | 6/2002 | Rabiner et al. |
| 2002/0188276 A1 | 12/2002 | Evans et al. |
| 2002/0189357 A1 | 12/2002 | Lai et al. |
| 2003/0009153 A1 | 1/2003 | Brisken et al. |
| 2003/0036705 A1 | 2/2003 | Hare et al. |
| 2003/0040762 A1 | 2/2003 | Dorros et al. |
| 2003/0199817 A1 | 10/2003 | Thompson et al. |
| 2003/0216732 A1 | 11/2003 | Truckai et al. |
| 2003/0225332 A1 | 12/2003 | Okada et al. |
| 2004/0019349 A1 | 1/2004 | Fuimaono et al. |
| 2004/0024393 A1 | 2/2004 | Nita et al. |
| 2004/0054367 A1 | 3/2004 | Teodoro, Jr. et al. |
| 2004/0164030 A1 | 8/2004 | Lowe et al. |
| 2004/0167511 A1 | 8/2004 | Buehlmann et al. |
| 2004/0171981 A1 * | 9/2004 | Rabiner ............ A61B 17/22012 604/20 |
| 2004/0193033 A1 | 9/2004 | Badehi et al. |
| 2005/0033311 A1 | 2/2005 | Guldfeldt et al. |
| 2005/0149110 A1 | 7/2005 | Wholey et al. |
| 2005/0165388 A1 | 7/2005 | Bhola |
| 2005/0171527 A1 | 8/2005 | Bhola |
| 2005/0228286 A1 | 10/2005 | Messerly et al. |
| 2006/0074441 A1 | 4/2006 | Mcguckin, Jr. et al. |
| 2006/0149169 A1 | 7/2006 | Nunomura et al. |
| 2006/0206039 A1 | 9/2006 | Wilson et al. |
| 2006/0264809 A1 | 11/2006 | Hansmann et al. |
| 2007/0032749 A1 | 2/2007 | Overall et al. |
| 2007/0161945 A1 | 7/2007 | Nita et al. |
| 2007/0178768 A1 | 8/2007 | Harshman et al. |
| 2008/0033284 A1 | 2/2008 | Hauck |
| 2008/0071343 A1 | 3/2008 | Mayberry et al. |
| 2008/0208084 A1 | 8/2008 | Horzewski et al. |
| 2008/0221506 A1 | 9/2008 | Rodriguez et al. |
| 2008/0294037 A1 | 11/2008 | Richter |
| 2009/0017293 A1 | 1/2009 | Arai et al. |
| 2009/0143795 A1 | 6/2009 | Robertson |
| 2010/0004558 A1 | 1/2010 | Frankhouser et al. |
| 2010/0023037 A1 | 1/2010 | Nita et al. |

(56) References Cited

U.S. PATENT DOCUMENTS

| | | |
|---|---|---|
| 2010/0069854 A1 | 3/2010 | Okoh et al. |
| 2010/0076454 A1 | 3/2010 | Bos |
| 2010/0121144 A1 | 5/2010 | Farhadi |
| 2010/0217306 A1 | 8/2010 | Raabe et al. |
| 2010/0268206 A1 | 10/2010 | Manwaring et al. |
| 2011/0046522 A1 | 2/2011 | Chan et al. |
| 2011/0105960 A1 | 5/2011 | Wallace |
| 2011/0130834 A1 | 6/2011 | Wilson et al. |
| 2011/0196399 A1 | 8/2011 | Robertson et al. |
| 2011/0196403 A1 | 8/2011 | Robertson et al. |
| 2011/0237982 A1 | 9/2011 | Wallace |
| 2011/0313328 A1 | 12/2011 | Nita |
| 2012/0010506 A1 | 1/2012 | Ullrich |
| 2012/0109021 A1 | 5/2012 | Hastings et al. |
| 2012/0130475 A1 | 5/2012 | Shaw |
| 2012/0217306 A1 | 8/2012 | Morrill Webb et al. |
| 2012/0238916 A1 | 9/2012 | Nita et al. |
| 2012/0238946 A1 | 9/2012 | Nita et al. |
| 2012/0311844 A1 | 12/2012 | Nita et al. |
| 2012/0330196 A1 | 12/2012 | Nita |
| 2013/0046297 A1 | 2/2013 | Lingeman et al. |
| 2013/0060169 A1 | 3/2013 | Yamada |
| 2013/0331652 A1 | 12/2013 | Okamoto |
| 2013/0338580 A1 | 12/2013 | Kamatani et al. |
| 2014/0005706 A1 | 1/2014 | Gelfand et al. |
| 2014/0012087 A1 | 1/2014 | Omoto |
| 2014/0039491 A1 | 2/2014 | Bakos et al. |
| 2014/0171804 A1 | 6/2014 | Van Hoven |
| 2014/0236118 A1 | 8/2014 | Unser et al. |
| 2014/0243712 A1 | 8/2014 | Humayun et al. |
| 2014/0350401 A1 | 11/2014 | Sinelnikov |
| 2014/0358028 A1 | 12/2014 | Vetter et al. |
| 2014/0358029 A1 | 12/2014 | Vetter et al. |
| 2015/0025544 A1 | 1/2015 | Nita et al. |
| 2015/0073357 A1 | 3/2015 | Bagwell et al. |
| 2015/0105621 A1 | 4/2015 | Farhadi |
| 2015/0105715 A1 | 4/2015 | Pikus et al. |
| 2015/0133918 A1 | 5/2015 | Sachar |
| 2015/0148795 A1 | 5/2015 | Amos et al. |
| 2015/0157443 A1 | 6/2015 | Hauser et al. |
| 2015/0190660 A1 | 7/2015 | Sarge et al. |
| 2015/0297258 A1 | 10/2015 | Escudero et al. |
| 2015/0359651 A1 | 12/2015 | Wübbeling |
| 2016/0128717 A1 | 5/2016 | Nita |
| 2016/0128767 A1 | 5/2016 | Azamian et al. |
| 2016/0135835 A1 | 5/2016 | Onuma |
| 2016/0183956 A1 | 6/2016 | Nita |
| 2016/0271362 A1 | 9/2016 | Van Liere |
| 2016/0328998 A1 | 11/2016 | Nita et al. |
| 2016/0338722 A1 | 11/2016 | Nita et al. |
| 2016/0367284 A1 | 12/2016 | Nita et al. |
| 2017/0065288 A1 | 3/2017 | Imai et al. |
| 2017/0128090 A1 | 5/2017 | Sarge |
| 2017/0224375 A1 | 8/2017 | Robertson et al. |
| 2017/0265879 A1 | 9/2017 | Washburn, II et al. |
| 2017/0265886 A1 | 9/2017 | Nita et al. |
| 2017/0354428 A1 | 12/2017 | Nita et al. |
| 2018/0042636 A1 | 2/2018 | Nita |
| 2018/0140321 A1 | 5/2018 | Deepa |
| 2018/0168668 A1 | 6/2018 | Zheng |
| 2018/0177515 A1 | 6/2018 | Boyle et al. |
| 2018/0197856 A1 | 7/2018 | Chou et al. |
| 2018/0221040 A1 | 8/2018 | Roll Hoye |
| 2018/0280005 A1 | 10/2018 | Parmentier |
| 2018/0280044 A1 | 10/2018 | Nita et al. |

FOREIGN PATENT DOCUMENTS

| | | |
|---|---|---|
| DE | 2438648 A1 | 2/1976 |
| DE | 8910040 U1 | 12/1989 |
| DE | 3821836 A1 | 1/1990 |
| DE | 1042435 C2 | 2/1994 |
| DE | 10146011 A1 | 4/2003 |
| EP | 0005719 A1 | 12/1979 |
| EP | 0316789 A2 | 5/1989 |
| EP | 0316796 A2 | 5/1989 |
| EP | 0376562 A2 | 7/1990 |
| EP | 0379156 A2 | 7/1990 |
| EP | 0394583 A2 | 10/1990 |
| EP | 0443256 A1 | 8/1991 |
| EP | 0472368 A2 | 2/1992 |
| EP | 0541249 A2 | 5/1993 |
| EP | 0820728 A2 | 1/1998 |
| EP | 1323481 A2 | 7/2003 |
| GB | 1106957 | 3/1968 |
| JP | H2-7150 U | 10/1988 |
| JP | 01-099547 | 4/1989 |
| JP | 6086822 A | 3/1994 |
| JP | H07500752 A | 1/1995 |
| JP | 7116260 A | 5/1995 |
| JP | 9-503137 | 3/1997 |
| JP | 10-216140 | 8/1998 |
| JP | 2000-291543 | 10/2000 |
| JP | 2001-104356 | 4/2001 |
| JP | 2001-321388 | 11/2001 |
| JP | 2002-186627 | 7/2002 |
| JP | 2005-253874 | 9/2005 |
| JP | 2006-522644 A | 10/2006 |
| JP | 2007512087 A | 5/2007 |
| JP | 2007520255 A | 7/2007 |
| WO | 8705739 A1 | 9/1987 |
| WO | 8705793 A1 | 10/1987 |
| WO | 8906515 A1 | 7/1989 |
| WO | 9001300 A1 | 2/1990 |
| WO | 9004362 A1 | 5/1990 |
| WO | 9107917 A2 | 6/1991 |
| WO | 9211815 A2 | 7/1992 |
| WO | 9308750 A2 | 5/1993 |
| WO | 9316646 A1 | 9/1993 |
| WO | 9412140 A1 | 6/1994 |
| WO | 9414382 A1 | 7/1994 |
| WO | 9508954 A1 | 4/1995 |
| WO | 9509571 A1 | 4/1995 |
| WO | 9515192 A1 | 6/1995 |
| WO | 9635469 A1 | 11/1996 |
| WO | 9705739 A1 | 2/1997 |
| WO | 9721462 A1 | 6/1997 |
| WO | 9745078 A1 | 12/1997 |
| WO | 9827874 A1 | 7/1998 |
| WO | 9835721 A2 | 8/1998 |
| WO | 9851224 A2 | 11/1998 |
| WO | 9852637 A1 | 11/1998 |
| WO | 9925412 A2 | 5/1999 |
| WO | 9053341 A1 | 9/2000 |
| WO | 9067830 A1 | 11/2000 |
| WO | 02094103 A1 | 11/2002 |
| WO | 93039381 A1 | 5/2003 |
| WO | 2004012609 A1 | 2/2004 |
| WO | 2004093736 A2 | 11/2004 |
| WO | 2004112888 A2 | 12/2004 |
| WO | 2005053769 A2 | 6/2005 |
| WO | 2005112770 A1 | 12/2005 |
| WO | 2006049593 A1 | 5/2006 |
| WO | 2013109269 A1 | 7/2013 |
| WO | 2014022716 A2 | 2/2014 |
| WO | 2014105754 A1 | 7/2014 |
| WO | 2014106847 A1 | 7/2014 |
| WO | 2018097856 A1 | 5/2018 |
| WO | 20180187159 A1 | 10/2018 |

OTHER PUBLICATIONS

Definition of the term "coupled", retrieved on May 18, 2013. <http://www.merriam-webster.com/dictionary/couple> 1 page total.

"E-Beam Theory" RDI-IBA Technology Group, downloaded from web on Oct. 8, 2002 <http://www.e-beamrdi/EbeamTheory.htm> 2 pages total.

Office Action dated May 20, 2010 from Japanese Application No. 2006-541200 filed on Oct. 25, 2004.

Office Action dated Oct. 11, 2012 from Japanese Application No. 2010-181956.

(56) References Cited

OTHER PUBLICATIONS

Noone, D.: Experimental and Numerical Investigation of Wire Waveguides for Therapeutic Ultrasound Angioplasty. M.Eng. Dublin City University. 2008.
Definition of the term "connected", retrieved on Sep. 21, 2013. <www.thefreedictionary.com/connected> 1 page total.
Supplemental European Search Report dated Nov. 5, 2009 for European Application No. EP03766931.
International Search Report dated Oct. 28, 2003 for PCT Application No. PCT/US2003/023468.
Extended European Search Report dated Mar. 22, 2012 for European Application No. EP11188799.
International Search Report dated Dec. 23, 2005 for PCT Application No. PCT/US2004/019378.
Extended European Search Report for Patent Application No. 06718204.8, dated May 30, 2012.
International Search Report dated Aug. 1, 2013 for PCT Application No. PCT/US2013/053306.
International Preliminary Report dated Aug. 1, 2013 for PCT Application No. PCT/US2013/053306.
Written Opinion dated Aug. 1, 2013 for PCT Application No. PCT/US2013/053306.
Supplemental European Search Report dated Apr. 29, 2009 for European Application No. EP04711207.3.
Office Action dated Aug. 3, 2010 from Japanese Application No. 2006-517355 filed on Jun. 16, 2004.
Office Action dated Jan. 26, 2010 from Japanese Application No. 2006-517355 filed on Jun. 16, 2004.
International Preliminary Report and Written Opinion dated Aug. 1, 2017 for PCT Application No. PCT/US2017/030675.
International Preliminary Report and Written Opinion dated Feb. 6, 2018 for PCT Application No. PCT/US2018/017022.
Extended European Search Report dated Mar. 5, 2012 for European Application No. 12153606.4-1269.
Margaret Fyfe et al., Mast cell degranulation and increased vascular permeability induced by therapeutic' ultrasound in the rate ankle joint, Br. J. exp Path., 1984, vol. 65, pp. 671-676.
"Irradiation, Biological, and Other Technologies: E-beam, Biological, and Sharps Treatment Systems", Non-Incineration Medical Waste Treatment Technologies, Aug. 2001, Chapter 9, pp. 69-74, Health Care Without Harm, Washington, DC.
Paul Yock et al., Catheter-Based Ultrasound Thrombolysis Shake, Rattle, and Reperfuse, https://doi.org/10 1161/01.CIR.95.6 1360 Circulation. 1997;95:1360-1362 Originally published Mar. 18, 1997.
Japanese Office Action for Japanese Application No. 2010-134566, dated Mar. 2, 2012.
Sehgal, et al., Ultrasound-Assisted Thrombolysis, Investigative Radiology, 1993, vol. 28, Issue 10, pp. 939-943.
Siegel, et al., "In Vivo Ultrasound Arterial Recanalization of Atherosclerotic Total Occlusions", Journal of the American College of Cardiology, Feb. 1990, vol. 15, No. 2, pp. 345-351.
"What is Electron Beam Curing?" downloaded from web on Nov. 14, 2002, 4 pages total. <http://www.ms.oml.gov/researchgroups/composites/new%20orccmt%20pages/pages/ebwha>.
EP Extended Search Report dated Aug. 13, 2009; Application 04710537.5-1269, 5 pages.

\* cited by examiner

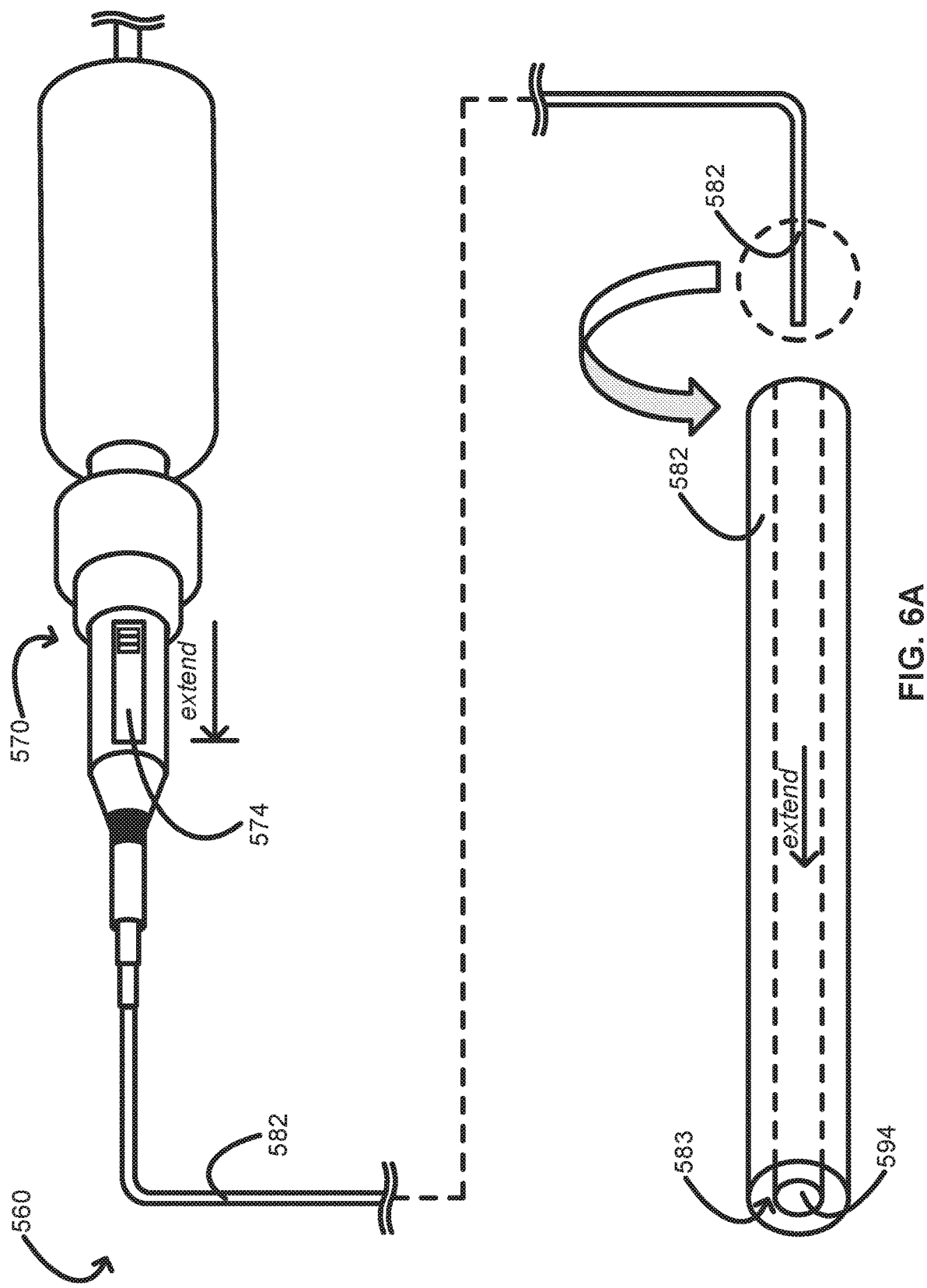

CATHETER WITH RETRACTABLE SHEATH AND METHODS THEREOF

PRIORITY

This application is a U.S. national phase of International Application No. PCT/US2017/060195, filed Nov. 6, 2017, which claims the benefit of priority to U.S. patent application Ser. No. 15/360,834, filed Nov. 23, 2016, which is incorporated by reference in its entirety herein.

FIELD

This application generally relates to catheters with retractable sheaths. In some embodiments, for example, the catheters are for modification of one or more intravascular lesions associated with atherosclerosis.

BACKGROUND

Atherosclerosis is characterized by one or more intravascular lesions formed in part of plaque including blood-borne substances such as fat, cholesterol, and calcium. An intravascular lesion such as an arterial lesion can form on a wall of an arterial lumen and build out across the lumen to an opposite wall thereof. A last point of patency often occurs at a boundary between the arterial lesion and the opposite wall of the arterial lumen.

Surgical procedures for atherosclerosis such as angioplasty or atherectomy can be used to restore patency and blood flow lost to the one or more intravascular lesions. To effect such surgical procedures, one or more endoluminal devices are advanced to an intravascular lesion to modify the intravascular lesion. For example, atherectomy can involve placing a guidewire through an intravascular lesion with a first, lesion-crossing device and subsequently advancing a second, atherectomy device to the intravascular lesion for ablation thereof. However, advancing an endoluminal device to an intravascular lesion can lead to device complications, surgical complications, or a combination thereof especially when a lesion-modifying tip of the endoluminal device is exposed before needed for a surgical procedure. Accordingly, there is a need to conceal lesion-modifying tips of endoluminal devices until needed for surgical procedures. Provided herein in some embodiments are systems and methods that address the foregoing.

SUMMARY

Provided herein in some embodiments is a system including a catheter assembly. The catheter assembly can include a housing, a sheath, and a core wire disposed within a sheath lumen. The housing can include a retraction-extension mechanism configured to retract the sheath from a first, fully extended position of the sheath, in which position a distal portion of the core wire can be wholly disposed within the sheath lumen. The housing can accommodate a proximal length of the sheath, and the retraction-extension mechanism can be configured to retract the proximal length of the sheath into the housing and expose a working length of a distal portion of the core wire. The core wire can include a sonic connector at a proximal end of the core wire configured to connect to an ultrasound-producing mechanism for ultrasound-based modification of one or more intravascular lesions with the working length of the core wire.

These and other features of the concepts provided herein may be better understood with reference to the drawings, description, and appended claims.

DRAWINGS

FIG. 1 provides a schematic illustrating a system in accordance with some embodiments.

Figure 2A:
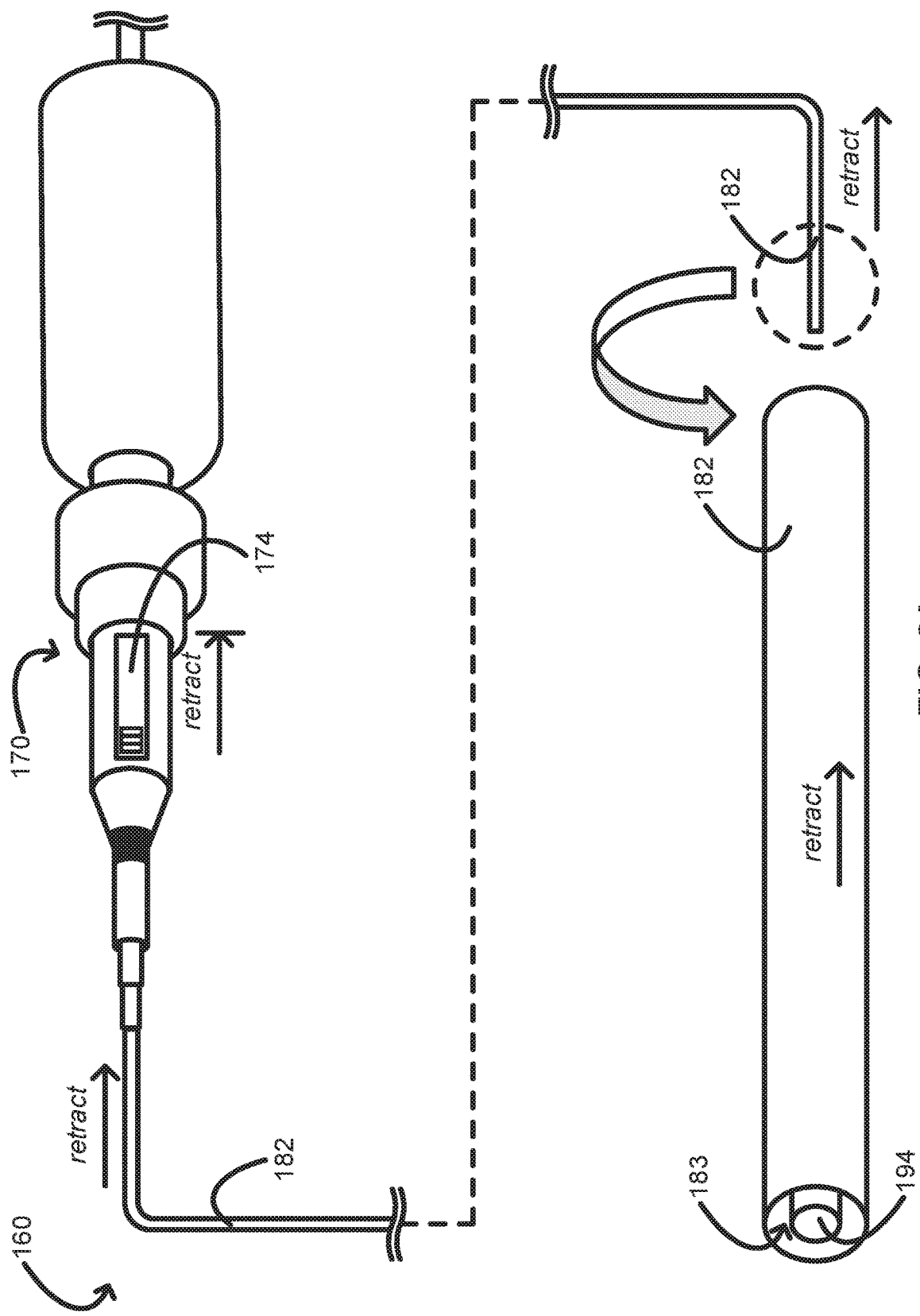

FIG. 2A provides a schematic illustrating a catheter assembly with a retraction-extension mechanism configured to retract a sheath from a first, fully extended position of the sheath in accordance with some embodiments.

Figure 2B:
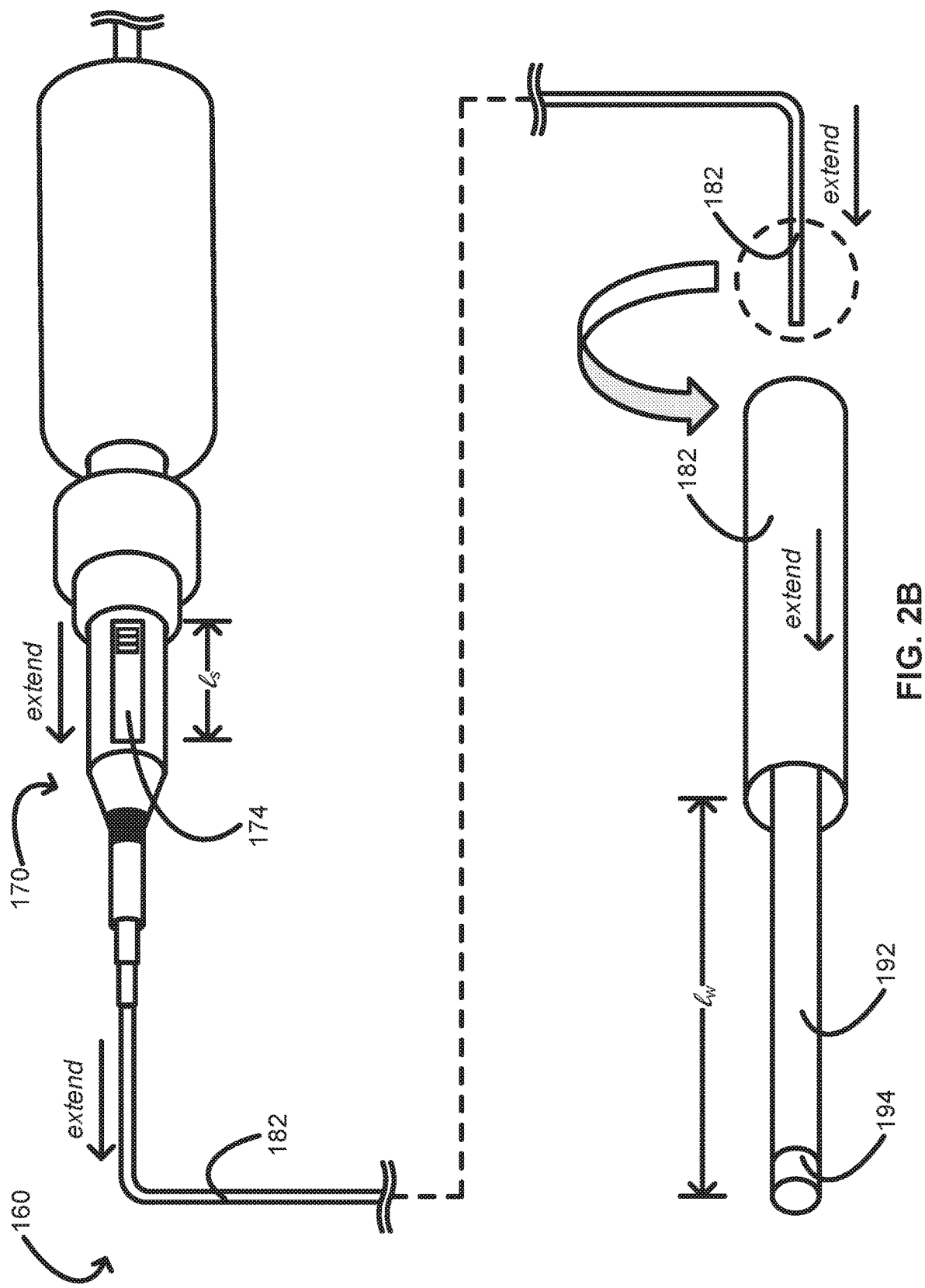

FIG. 2B provides a schematic illustrating a catheter assembly with a retraction-extension mechanism configured to extend a sheath from a second, fully retracted position of the sheath in accordance with some embodiments.

Figure 3A:
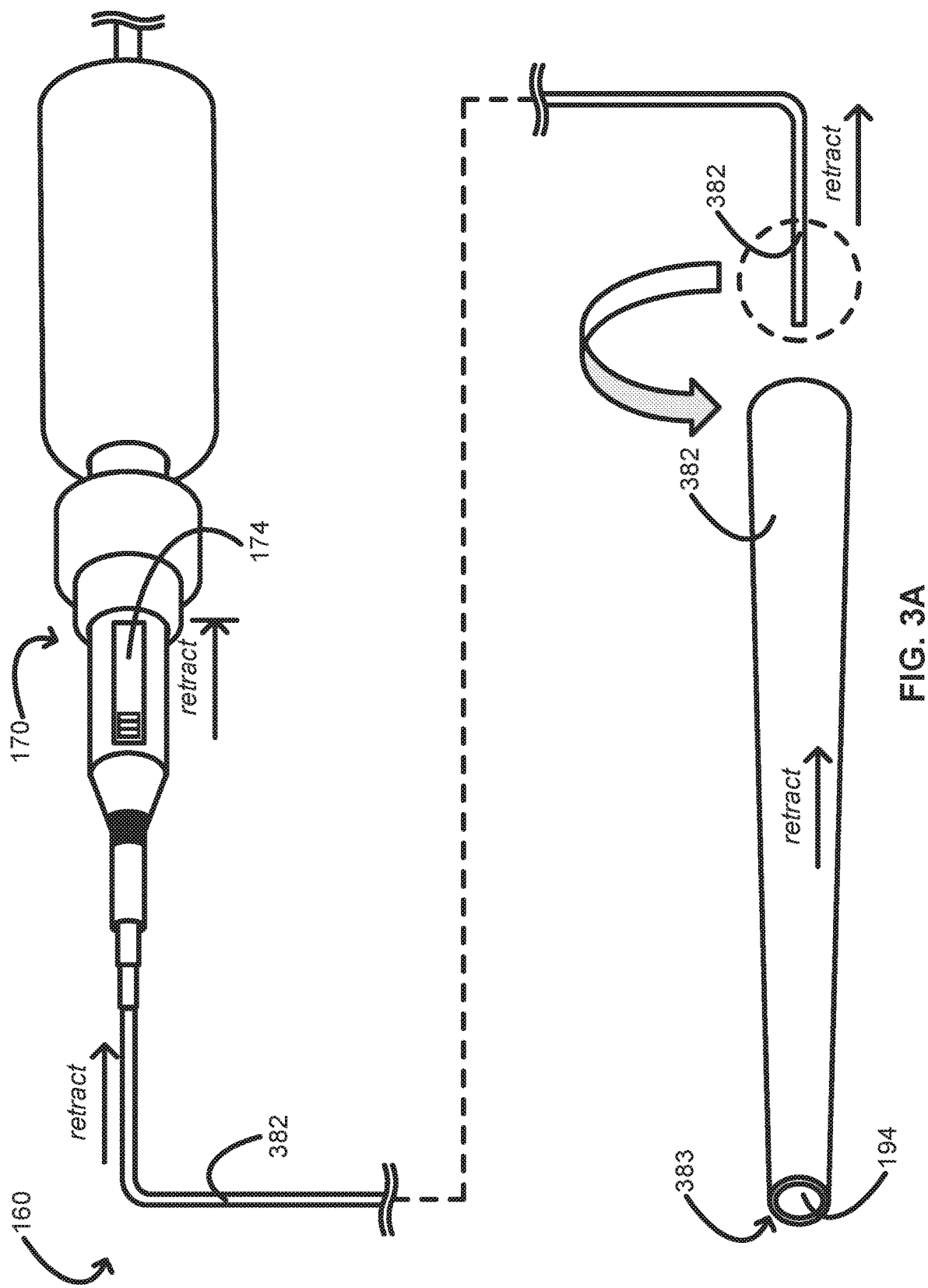

FIG. 3A provides a schematic illustrating a catheter assembly with a retraction-extension mechanism configured to retract a tapered sheath from a first, fully extended position of the sheath in accordance with some embodiments.

Figure 3B:
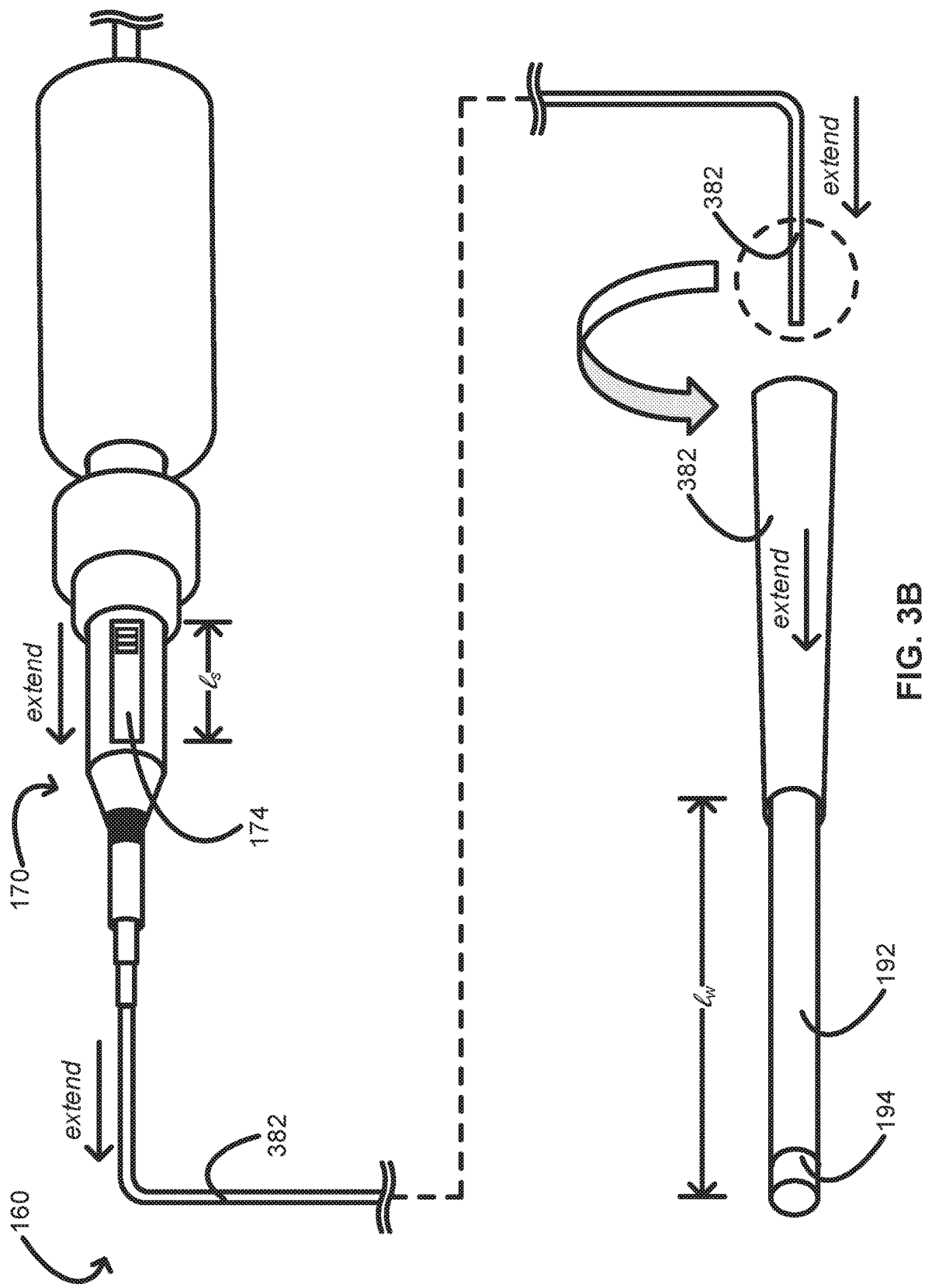

FIG. 3B provides a schematic illustrating a catheter assembly with a retraction-extension mechanism configured to extend a tapered sheath from a second, fully retracted position of the sheath in accordance with some embodiments.

Figure 4A:
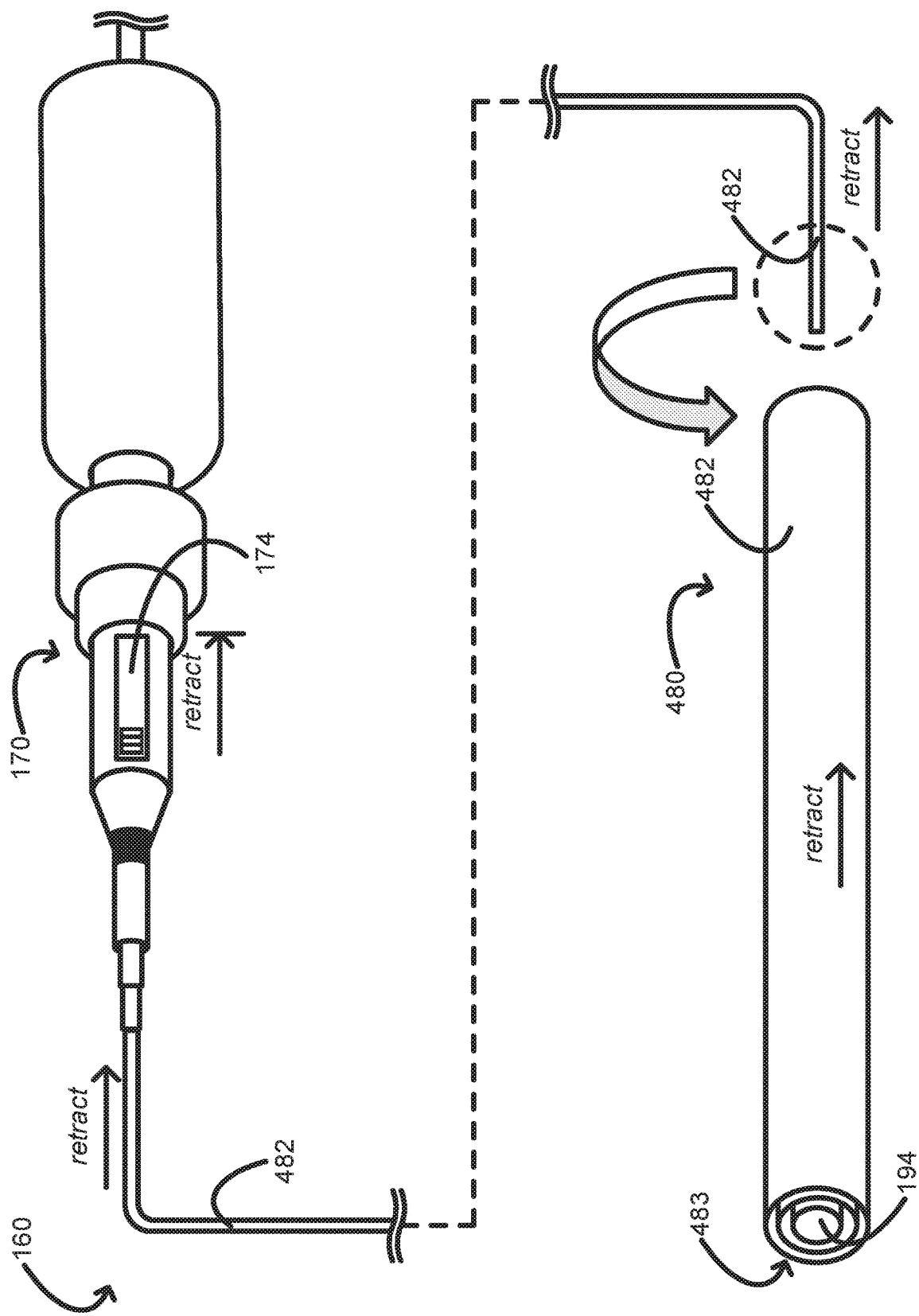

FIG. 4A provides a schematic illustrating a catheter assembly with a retraction-extension mechanism configured to retract a sheath of a telescopic system from a first, fully extended position of the sheath in accordance with some embodiments.

Figure 4B:
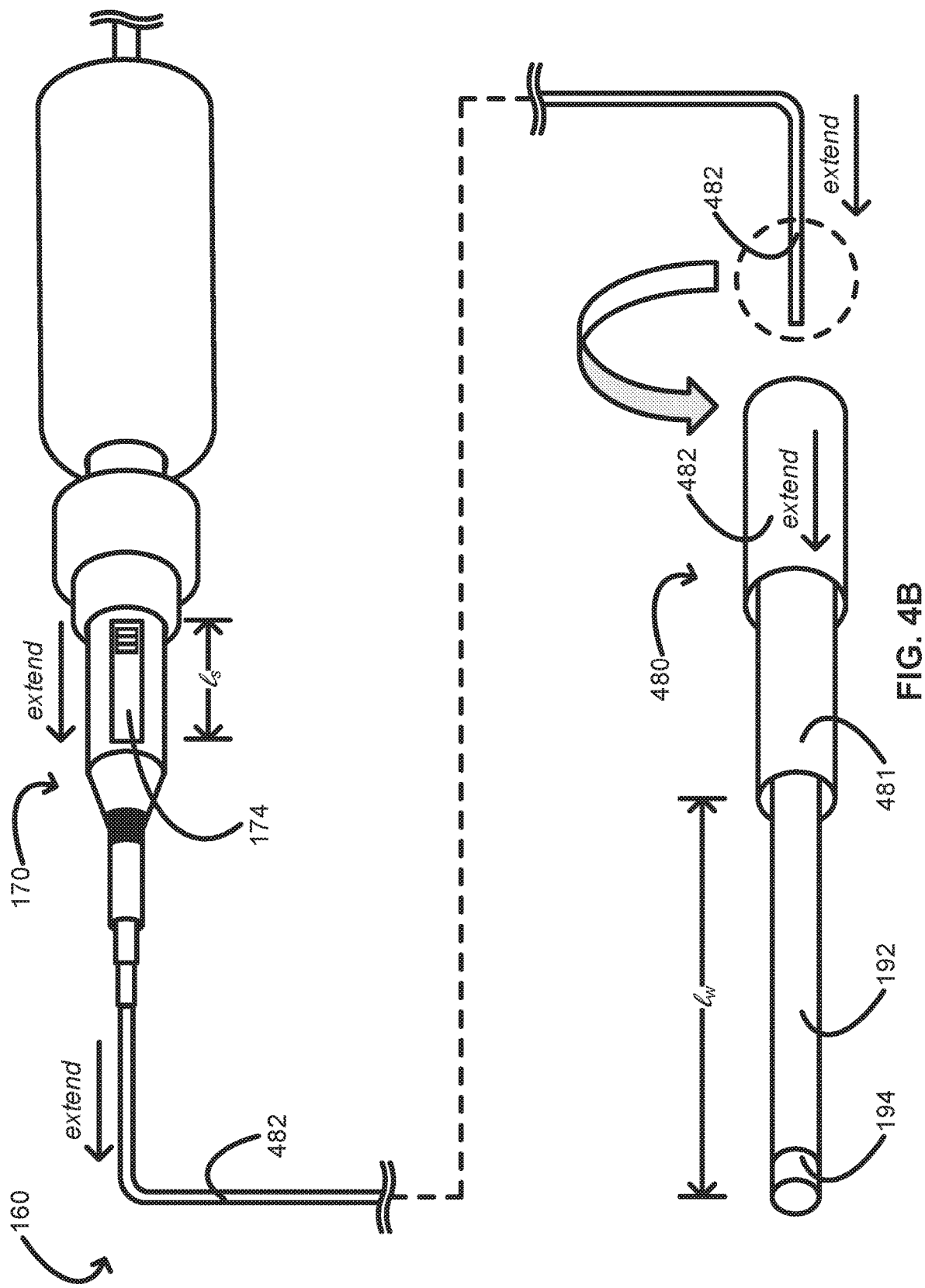

FIG. 4B provides a schematic illustrating a catheter assembly with a retraction-extension mechanism configured to extend a sheath of a telescopic system from a second, fully retracted position of the sheath in accordance with some embodiments.

Figure 5:
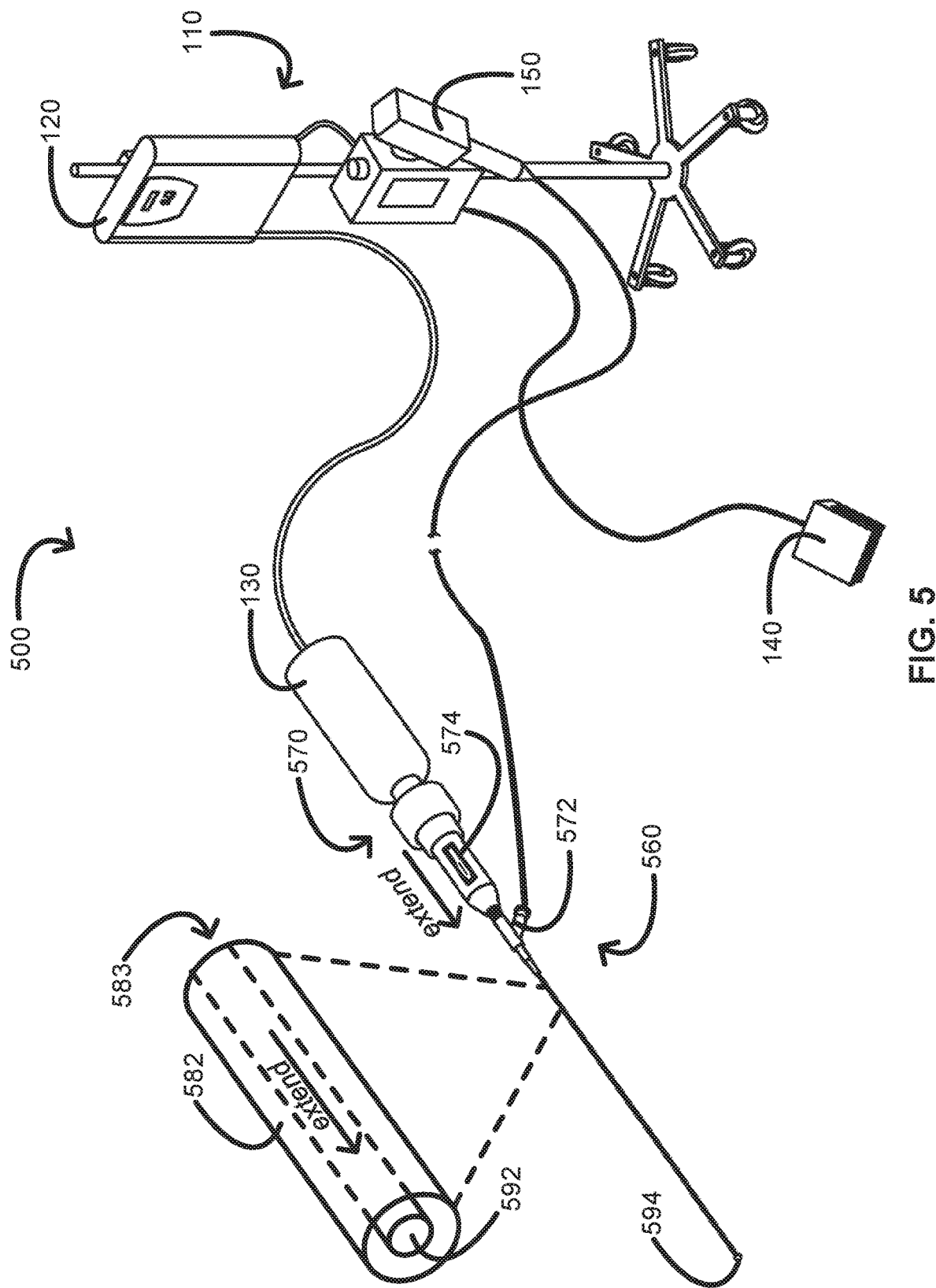

FIG. 5 provides a schematic illustrating an alternative system in accordance with some embodiments.

FIG. 6A provides a schematic illustrating a catheter assembly with an extension-retraction mechanism configured to extend a core wire from a first, fully retracted position of the core wire in accordance with some embodiments.

Figure 6B:
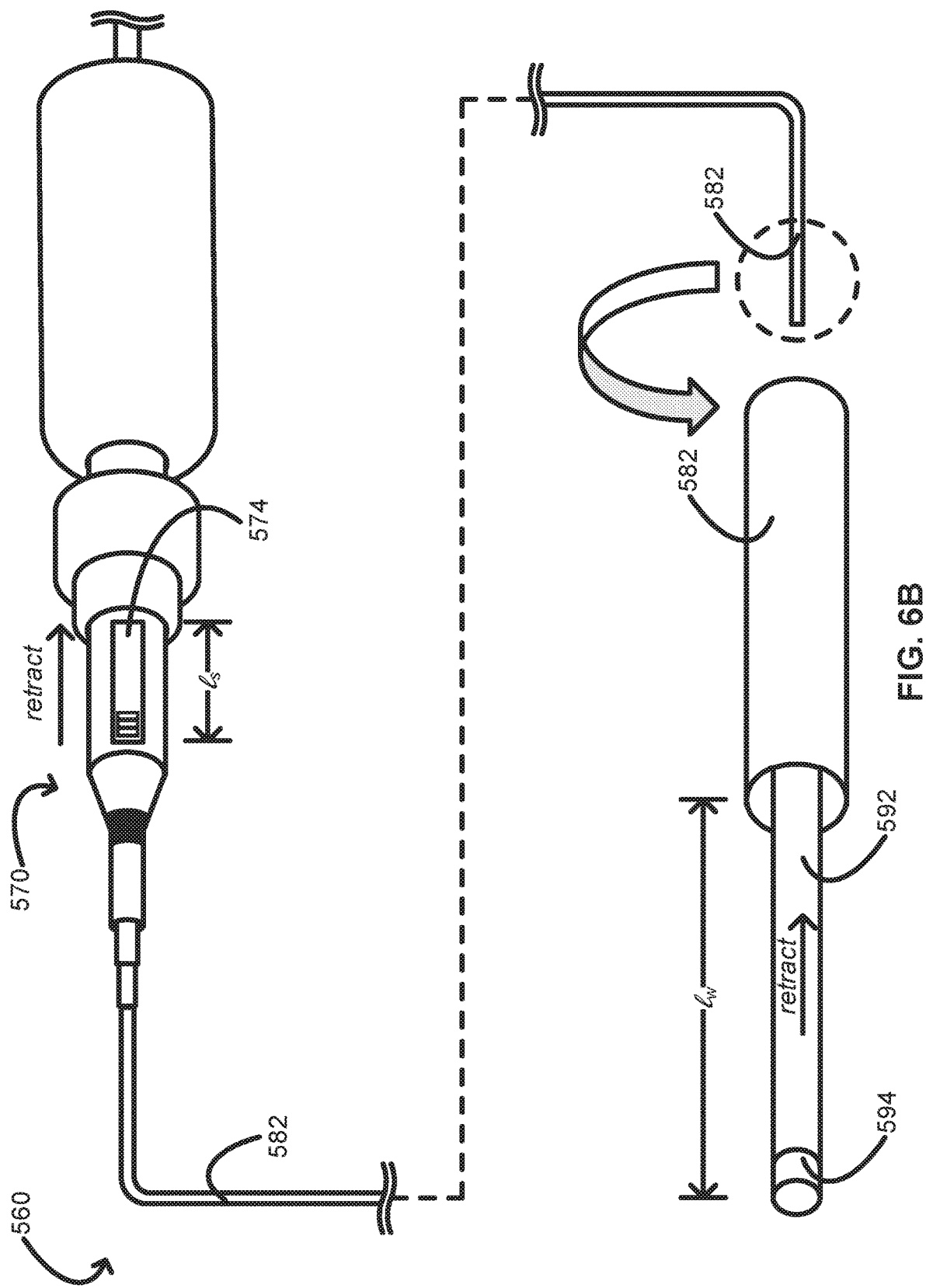

FIG. 6B provides a schematic illustrating a catheter assembly with an extension-retraction mechanism configured to retract a core wire from a second, fully extended position of the core wire in accordance with some embodiments.

DESCRIPTION

Before some particular embodiments are provided in greater detail, it should be understood that the particular embodiments provided herein do not limit the scope of the concepts provided herein. It should also be understood that a particular embodiment provided herein can have features that can be readily separated from the particular embodiment and optionally combined with or substituted for features of any of a number of other embodiments provided herein.

Regarding terminology used herein, it should also be understood the terminology is for the purpose of describing some particular embodiments, and the terminology does not limit the scope of the concepts provided herein. Unless indicated otherwise, ordinal numbers (e.g., first, second, third, etc. are used to distinguish or identify different features or steps in a group of features or steps, and do not supply a serial or numerical limitation. For example, "first,"

"second," and "third" features or steps need not necessarily appear in that order, and the particular embodiments including such features or steps need not necessarily be limited to the three features or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

With respect to "proximal," a "proximal portion" of, for example, a sheath or a core wire respectively includes a portion of the sheath or the core wire proximate to a system operator when the system is used as intended. Likewise, a "proximal length" of, for example, the sheath or the core wire respectively includes a length of the sheath or the core wire proximate to the system operator when the system is used as intended. A "proximal end" of, for example, the sheath or the core wire respectively includes an end of the sheath or the core wire proximate to the system operator when the system is used as intended. The proximal portion or the proximal length of the sheath or the core wire can respectively include the proximal end of the sheath or the core wire; however, the proximal portion or the proximal length of the sheath or the core wire need not respectively include the proximal end of the sheath or the core wire. That is, unless context suggests otherwise, the proximal portion or the proximal length of the sheath or the core wire is respectively not a terminal portion or a terminal length of the sheath of the core wire.

With respect to "distal," a "distal portion" of, for example, a sheath or a core wire respectively includes a portion of the sheath or the core wire proximate to a patient when the system is used as intended. Likewise, a "distal length" of, for example, the sheath or the core wire respectively includes a length of the sheath or the core wire proximate to the patient when the system is used as intended. A "distal end" of, for example, the sheath or the core wire respectively includes an end of the sheath or the core wire proximate to the patient when the system is used as intended. The distal portion or the distal length of the sheath or the core wire can respectively include the distal end of the sheath or the core wire; however, the distal portion or the distal length of the sheath or the core wire need not respectively include the distal end of the sheath or the core wire. That is, unless context suggests otherwise, the distal portion or the distal length of the sheath or the core wire is respectively not a terminal portion or a terminal length of the sheath of the core wire.

Unless defined otherwise, all technical and scientific terms used herein have the same meaning as commonly understood those of ordinary skill in the art.

Surgical procedures for atherosclerosis such as angioplasty or atherectomy can be used to restore patency and blood flow lost to the one or more intravascular lesions. To effect such surgical procedures, one or more endoluminal devices are advanced to an intravascular lesion to modify the intravascular lesion. For example, atherectomy can involve placing a guidewire through an intravascular lesion with a first, lesion-crossing device and subsequently advancing a second, atherectomy device to the intravascular lesion for ablation thereof. However, advancing an endoluminal device to an intravascular lesion can lead to device complications, surgical complications, or a combination thereof especially when a lesion-modifying tip of the endoluminal device is exposed before needed for a surgical procedure. Accordingly, there is a need to conceal lesion-modifying tips of endoluminal devices until needed for surgical procedures. Provided herein in some embodiments are systems and methods that address the foregoing.

For example, provided herein in some embodiments is a system including a catheter assembly. The catheter assembly can include a housing, a sheath, and a core wire disposed within a sheath lumen. The housing can include a retraction-extension mechanism configured to retract the sheath from a first, fully extended position of the sheath, in which position a distal portion of the core wire can be wholly disposed within the sheath lumen. The housing can accommodate a proximal length of the sheath, and the retraction-extension mechanism can be configured to retract the proximal length of the sheath into the housing and expose a working length of a distal portion of the core wire. The core wire can include a sonic connector at a proximal end of the core wire configured to connect to an ultrasound-producing mechanism for ultrasound-based modification of one or more intravascular lesions with the working length of the core wire.

FIG. 1 provides a schematic illustrating a system 100 in accordance with some embodiments. The system 100 can be configured for crossing one or more intravascular lesions, ablating one or more intravascular lesions, or a combination thereof.

As shown in FIG. 1, the system 100 can include a console 110. The console 110 provides a system operator an instrument for monitoring and controlling the system 100 and various sub-systems and functions thereof. The console 110 can include an ultrasound-producing mechanism including an ultrasound generator 120 and an ultrasound transducer 130. The ultrasound-producing mechanism can be configured to convert an electric current into a vibrational energy. For example, the ultrasound generator 120 can be configured to convert an alternating electric current (e.g., a current associated with mains electricity) into a high-frequency current (e.g., a current with a frequency commensurate with the operating frequency of the ultrasound transducer 130), and the ultrasound transducer 130, in turn, can be configured to convert the high-frequency current into the vibrational energy (e.g., >20 kHz such as 20.5 kHz±500 Hz).

In some embodiments, the console 110 can further include a foot switch 140 configured to activate and deactivate the system 100 such as activate and deactivate a core wire 192 of a catheter assembly 160. For example, when the system 100 is powered on but not activated, the foot switch 140 can be used to activate the system 100, thereby activating the core wire 192 of the catheter assembly 160. When the system 100 is powered on and activated, the foot switch 140 can be used to deactivate the system 100, thereby deactivating the core wire 192 of the catheter assembly 160. In some embodiments, the console 110 can further include an injector 150 configured to inject an irrigant into an optional irrigation lumen 172 of the catheter assembly 160. The irrigant can be, for example, sterile saline for irrigating an anatomical area undergoing an intravascular lesion-modification procedure (e.g., crossing an intravascular lesion, ablating an intravascular lesion, etc.), for cooling the core wire 192 of the catheter assembly 160, or a combination thereof. In some embodiments, the console 110 can further include the foot switch 140 and the injector 150. In such embodiments, the foot switch 140 can be further configured to activate and deactivate the injector 150 when the system 100 is respectively activated and deactivated with the foot switch 140.

As shown in FIG. 1, the system 100 can also include the aforementioned catheter assembly 160. The catheter assembly 160 can include a housing 170, a sheath 182, and the aforementioned core wire 192 disposed within a sheath lumen 183. The housing 170 can include a retraction-extension mechanism 174 configured to retract the sheath 182 from a first, fully extended position of the sheath 182. In the fully extended position of the sheath, a distal portion of the core wire 192 including i) a lesion-modifying tip 194 of the core wire 192, or ii) a lesion-modifying tip member 194 coupled to the core wire 192, can be wholly disposed within the sheath lumen 183. (See FIG. 2A for more detail.) The retraction-extension mechanism 174 can be further configured to extend the sheath 182 from a second, fully retracted position of the sheath 182. In the fully retracted position, a maximum working length $l_{w(max)}$ (see FIG. 2B for $l_w$) of the core wire 192 including i) the lesion-modifying tip 194 of the core wire 192 or ii) the lesion-modifying tip member 194 coupled to the core wire 192 can be exposed outside the sheath lumen 183. (See FIG. 2B for more detail.)

FIG. 2A provides a schematic illustrating the catheter assembly 160 with the retraction-extension mechanism 174 configured to retract the sheath 182 from the first, fully extended position of the sheath 182 in accordance with some embodiments. As shown in FIG. 2A, the housing 170 of the catheter assembly 160 can include the retraction-extension mechanism 174 configured to retract the sheath 182 from the first, fully extended position of the sheath 182. The distal portion of the core wire 192 exemplified at least in part by the blown-up portion of the sheath 182 and the core wire 192 in FIG. 2A can be wholly disposed with the lesion-modifying tip or tip member 194 within the sheath lumen 183 in the fully extended position of the sheath 182.

FIG. 2B provides a schematic illustrating the catheter assembly 160 with the retraction-extension mechanism 174 configured to extend the sheath 182 from the second, fully retracted position of the sheath 182 in accordance with some embodiments. As shown in FIG. 2B, the housing 170 of the catheter assembly 160 can include the retraction-extension mechanism 174 also configured to extend the sheath 182 from the second, fully retracted position of the sheath 182. The maximum working length $l_{w(max)}$ of the core wire 192 can be exposed with the lesion-modifying tip or tip member 194 outside the sheath lumen 183 in the fully retracted position of the sheath 182.

As shown in FIGS. 2A and 2B, the housing 170 can accommodate a proximal length of the sheath 182, and the retraction-extension mechanism 174 can be configured to retract the proximal length of the sheath 182 into the housing 170 and expose the working length $l_w$ of the distal portion of the core wire 192 for ultrasound-based modification of one or more intravascular lesions with the working length $l_w$ of the core wire 192. A maximum working length $l_{w(max)}$ of the core wire 192 can be defined by a retraction distance over which a point on the sheath retracts from the first position to the second position. The maximum working length $l_{w(max)}$ of the core wire 192 can also be defined by a slot length $l_s$ in the housing 170 configured to accommodate the proximal length of the sheath 182 in the second position. The working length $l_w$ of the core wire 192 can range between about 5 and 200 mm, including between about 5 and 100 mm or between about 100 and 200 mm; however the working length $l_w$ of the core wire 192 is not limited thereto.

The retraction-extension mechanism 174 can be a hand-actuated retraction-extension mechanism, or the retraction-extension mechanism 174 can be a motor-actuated retraction-extension mechanism. Whether hand-actuated or motor-actuated, the retraction-extension mechanism 174 can be configured to i) retract the sheath 182 from the first, fully extended position of the sheath 182, ii) extend the sheath 182 from the second, fully retracted position of the sheath 182, iii) retract or extend the sheath 182 into intermediate positions between the first position and the second position, or iv) any combination thereof. Retraction and extension of the sheath 182 into the foregoing intermediate positions provides customizability as needed for different anatomy and intravascular lesions.

The core wire 192 can include a sonic connector (not shown) a proximal end of the core wire 192 configured to connect to an ultrasound-producing mechanism for ultrasound-based modification of one or more intravascular lesions with the working length $l_w$ of the core wire 192. The sonic connector can be configured to connect to the ultrasound-producing mechanism by the ultrasound transducer 130 or an intervening ultrasonic horn (not shown). A distal end of the core wire 192 can include the lesion-modifying tip 194 of the core wire 192, or the distal end of the core wire 192 can be coupled to the lesion-modifying tip member 194.

The working length $l_w$ of the distal portion of the core wire 192 beyond the sheath 182 or the sheath lumen 183 thereof can be configured for displacement to effect intravascular lesion modification. The displacement can be longitudinal, transverse, or longitudinal and transverse in accordance with a profile of the core wire 192 and the vibrational energy (e.g., >20 kHz such as 20.5 kHz±500 Hz). Longitudinal displacement of the working length $l_w$ of the core wire 192 can result in micromotion such as cavitation, and transverse displacement of the working length $l_w$ of the core wire 192 can result in macromotion. The micromotion can be used to cross intravascular lesions. The macromotion coupled with the micromotion can be used to ablate intravascular lesions, thereby breaking the lesions into minute fragments and restoring patency and blood flow.

FIGS. 3A, 3B, 4A and 4B provide schematics illustrating catheter assemblies with sheath alternatives to the sheath of FIGS. 2A and 2B in accordance with some embodiments.

FIG. 3A provides a schematic illustrating a catheter assembly 160 with a tapered sheath 382 and a retraction-extension mechanism 174 configured to retract the tapered sheath 382 from a first, fully extended position of the sheath 382 in accordance with some embodiments. FIG. 3B provides a schematic illustrating the catheter assembly 160 with the retraction-extension mechanism 174 configured to extend the tapered sheath 382 from a second, fully retracted position of the sheath 382 in accordance with some embodiments. The descriptions set forth above with respect to the features of FIGS. 2A and 2B are incorporated herein by reference to describe the features of FIGS. 3A and 3B, which use the same reference numerals as FIGS. 2A and 2B; however, as shown in FIGS. 3A and 3B, a distal portion of the sheath 382 can be tapered proximate to the working length $l_w$ of the core wire 192. A sheath lumen 383 of the tapered sheath 382 can have a constant diameter to accommodate the core wire 192 and the profile thereof.

FIG. 4A provides a schematic illustrating a catheter assembly 160 with a sheath 482 of a telescopic system 480 and a retraction-extension mechanism 174 configured to retract the sheath 482 of the telescopic system 480 from a first, fully extended position of the sheath 482 in accordance with some embodiments. FIG. 4B provides a schematic illustrating the catheter assembly 160 with the retraction-extension mechanism 174 configured to extend the sheath 482 of the telescopic system 480 from a second, fully retracted position of the sheath 482 in accordance with some embodiments. The descriptions set forth above with respect to the features of FIGS. 2A and 2B are incorporated herein by reference to describe the features of FIGS. 4A and 4B, which use the same reference numerals as FIGS. 2A and 2B; however, the catheter assembly 160 can further include a telescopic system 480 including two or more nested telescopic members such as a first telescopic member 481 and a second telescopic member 482. At least one telescopic member of the two or more telescopic members can be the sheath 482. As shown, the second telescopic member 482 can be the sheath 482. Alternatively, the two or more nested telescopic members such as the first telescopic member 481 and the second telescopic member 482, together, form the sheath 482. A sheath lumen 483 of the sheath 482 such as the foregoing sheath 482 formed of the first telescopic member 481 and the second telescopic member 482 can have a constant diameter to accommodate the core wire 192 and the profile thereof.

In an alternative to the foregoing telescopic system 480, the two or more nested telescopic members can be located in a proximal portion of the catheter assembly 160 proximate to the retraction-extension mechanism 174.

FIG. 5 provides a schematic illustrating an alternative system 500 in accordance with some embodiments. The system 500 can be configured for crossing one or more intravascular lesions, ablating one or more intravascular lesions, or a combination thereof.

The descriptions set forth above with respect to the features of HG 1 in common with the features of FIG. 5 are incorporated herein by reference, which features are readily identified by common reference numerals; however, as shown in FIG. 5, the system 500 is configured to extend and retract a core wire 592 of a catheter assembly 56 instead of retract and extend a sheath 582.

As shown in FIG. 5, the system 500 can include the aforementioned catheter assembly 560. The catheter assembly 560 can include a housing 570, the aforementioned sheath 582, the aforementioned core wire 592 disposed within a sheath lumen 583, and an optional irrigation lumen 572 for use with the injector 150. The housing 570 can include an extension-retractor mechanism 574 configured to extend the core wire 592 from a first, fully retracted position of the core wire 592. In the fully retracted position of the core wire 592, a distal portion of the core wire 592 including i) a lesion-modifying tip 594 of the core wire 592, or ii) a lesion-modifying tip member 594 coupled to the core wire 592, can be wholly disposed within the sheath lumen 583. (See FIG. 6A for more detail.) The extension-retraction mechanism 574 can be further configured to retract the core wire 592 from a second, fully extended position of the core wire 592. In the fully extended position, a maximum working length $l_{w(max)}$ (see FIG. 6B for $l_w$) of the core wire 592 including i) the lesion-modifying tip 594 of the core wire 592 or ii) the lesion-modifying tip member 594 coupled to the core wire 592 can be exposed outside the sheath lumen 583. (See FIG. 6B for more detail.)

FIG. 6A provides a schematic illustrating the catheter assembly 560 with the extension-retraction mechanism 574 configured to extend the core wire 592 from the first, fully retracted position of the core wire 592 in accordance with some embodiments. As shown in FIG. 6A, the housing 570 of the catheter assembly 560 can include the extension-retraction mechanism 574 configured to extend the core wire 592 from the first, fully retracted position of the core wire 592. The distal portion of the core wire 592—exemplified at least in part by the blown-up portion of the sheath 582 and the core wire 592 in FIG. 6A—can be wholly disposed with the lesion-modifying tip or tip member 594 within the sheath lumen 583 in the fully retracted position of the core wire 592.

FIG. 6B provides a schematic illustrating the catheter assembly 560 with the extension-retraction mechanism 574 configured to retract the core wire 592 from the second, fully extended position of the core wire 592 in accordance with some embodiments. As shown in FIG. 6B, the housing 570 of the catheter assembly 560 can include the extension-retraction mechanism 574 also configured to retract the core wire 592 from the second, fully extended position of the core wire 592. The maximum working length $l_{w(max)}$ of the core wire 592 can be exposed with the lesion-modifying tip or tip member 594 outside the sheath lumen 583 in the fully extended position of the core wire 592.

As shown in FIGS. 6A and 6B, the housing 570 can accommodate a proximal length of the core wire 592, and the extension-retraction mechanism 574 can be configured to extend the proximal length of the core wire 592 from the housing 570 and expose the working length $l_w$ of the distal portion of the core wire 592 for ultrasound-based modification of one or more intravascular lesions with the working length $l_w$ of the core wire 592. A maximum working length $l_{w(max)}$ of the core wire 592 can be defined by an extension distance over which a point on the core wire 592 extends from the first position to the second position. The maximum working length $l_{w(max)}$ of the core wire 592 can also be defined by a slot length $l_w$ in the housing 570 configured to accommodate the proximal length of the core wire 592 in the first position. The working length $l_w$ of the core wire 592 can range between about 5 and 200 mm, including between about 5 and 100 mm or between about 100 and 200 mm; however the working length $l_w$ of the core wire 592 is not limited thereto.

The extension-retraction mechanism 574 can be a hand-actuated extension-retraction mechanism, or the extension-retraction mechanism 574 can be a motor-actuated extension-retraction mechanism. Whether hand-actuated or motor-actuated, the extension-retraction mechanism 574 can be configured to i) extend the core wire 592 from the first, fully retracted position of the core wire 592, ii) retract the core wire 592 from the second, fully extended position of the core wire 592, iii) extend or retract the core wire 592 into intermediate positions between the first position and the second position, or iv) any combination thereof. Extension and retraction of the core wire 592 into the foregoing intermediate positions provides customizability as needed for different anatomy and intravascular lesions.

The core wire 592 can include a sonic connector (not shown) at a proximal end of the core wire 592 configured to connect to an ultrasound-producing mechanism for ultrasound-based modification of one or more intravascular lesions with the working length 6 of the core wire 592. The sonic connector can be configured to connect to the ultrasound-producing mechanism by the ultrasound transducer 130 or an intervening ultrasonic horn (not shown). A distal end of the core wire 592 can include the lesion-modifying tip 594 of the core wire 592, or the distal end of the core wire 592 can be coupled to the lesion-modifying tip member 594.

The working length $l_w$ of the distal portion of the core wire 592 beyond the sheath 582 or the sheath lumen 583 thereof can be configured for displacement to effect intravascular lesion modification. The displacement can be longitudinal, transverse, or longitudinal and transverse in accordance with a profile of the core wire 592 and the vibrational energy (e.g., >20 kHz such as 20.5 kHz±500 Hz). Longitudinal displacement of the working length & of the core wire 592 can result in micromotion such as cavitation, and transverse displacement of the working length $l_w$ of the core wire 592 can result in macromotion. The micromotion can be used to cross intravascular lesions. The macromotion coupled with the micromotion can be used to ablate intravascular lesions, thereby breaking the lesions into minute fragments and restoring patency and blood flow.

As such, provided herein in some embodiments is a system including a catheter assembly. The catheter assembly can include a housing, a sheath including a sheath lumen, and a core wire disposed within the sheath lumen. The housing can include a retraction-extension mechanism configured to retract the sheath from a first, fully extended position of the sheath and extend the sheath from a second, fully retracted position of the sheath. The retraction-extension mechanism can be further configured to retract a proximal length of the sheath into the housing and expose a working length of a distal portion of the core wire for ultrasound-based modification of one or more intravascular lesions.

In such embodiments, the distal portion of the core wire can be wholly disposed within the sheath lumen while the sheath is in the first position.

In such embodiments, a maximum working length of the core wire can be defined by a retraction distance over which a point on the sheath retracts from the first position to the second position. The retraction distance can be defined by a slot length in the housing configured to accommodate the proximal length of the sheath in the second position.

In such embodiments, a distal portion of the sheath can be tapered proximate to the working length of the core wire.

In such embodiments, the retraction-extension mechanism can be a hand-actuated or motor actuated retraction-extension mechanism.

In such embodiments, the catheter assembly can further include a telescopic system including two or more nested telescopic members. At least one telescopic member of the two or more telescopic members can be the sheath.

In such embodiments, the system can further include a console. The console can include an ultrasound-producing mechanism configured to convert an electric current into a vibrational energy. A sonic connector at a proximal end of the core wire can be configured to connect to the ultrasound-producing mechanism for the ultrasound-based modification of one or more intravascular lesions.

In such embodiments, the ultrasound-producing mechanism can include an ultrasonic generator, an ultrasonic transducer, and an ultrasonic horn. The ultrasonic generator can be configured to convert an alternating electric current into a high-frequency current. The ultrasonic transducer can be configured to convert the high-frequency current into the vibrational energy. The ultrasonic horn can be configured to augment an amplitude of the vibrational energy. The sonic connector of the core wire can be configured to connect to the ultrasonic horn for the ultrasound-based modification of one or more intravascular lesions.

Also provided herein in some embodiments is a system including a catheter assembly. The catheter assembly can include a housing, a sheath including a sheath lumen, and a core wire disposed within the sheath lumen. The housing can include a retraction-extension mechanism configured to retract the sheath from a first, fully extended position of the sheath, in which position a distal portion of the core wire can be wholly disposed within the sheath lumen. The retraction-extension mechanism can be further configured to extend the sheath from a second, fully retracted position of the sheath. The housing can accommodate a proximal length of the sheath, and the retraction-extension mechanism can be configured to retract the proximal length of the sheath into the housing and expose a working length of a distal portion of the core wire. The working length can be defined by a slot length in the housing configured to accommodate the proximal length of the sheath in the second position. The core wire can include a sonic connector at a proximal end of the core wire configured to connect to an ultrasound-producing mechanism for ultrasound-based modification of one or more intravascular lesions.

In such embodiments, a distal portion of the sheath can be tapered proximate to the working length of the core wire.

In such embodiments, the retraction-extension mechanism can be a hand-actuated or motor-actuated retraction-extension mechanism.

In such embodiments, the system can further include a console. The console can include an ultrasonic generator, an ultrasonic transducer, and an ultrasonic horn. The ultrasonic generator can be configured to convert an alternating electric current into a high-frequency current. The ultrasonic transducer can be configured to convert the high-frequency current into the vibrational energy. The ultrasonic horn can be configured to augment an amplitude of the vibrational energy. The sonic connector of the core wire can be configured to connect to the ultrasonic horn for the ultrasound-based modification of one or more intravascular lesions.

Also provided herein in some embodiments is a system including a catheter assembly and a console. The catheter assembly can include a housing, a sheath including a sheath lumen, and a core wire disposed within the sheath lumen. The housing can include a retraction-extension mechanism configured to retract the sheath from a first, fully extended position of the sheath, in which position a distal portion of the core wire can be wholly disposed within the sheath lumen. The retraction-extension mechanism can be further configured to extend the sheath from a second, fully retracted position of the sheath. The housing can accommodate a proximal length of the sheath, and the retraction-extension mechanism can be configured to retract the proximal length of the sheath into the housing and expose a working length of a distal portion of the core wire for ultrasound-based modification of one or more intravascular lesions. The console can include an ultrasound-producing mechanism configured to convert an electric current into a vibrational energy. A sonic connector at a proximal end of the core wire can be configured to connect to the ultrasound-producing mechanism for the ultrasound-based modification of one or more intravascular lesions.

In such embodiments, a maximum working length of the core wire can be defined by a retraction distance over which a point on the sheath retracts from the first position to the second position.

In such embodiments, a maximum working length of the core wire can be defined by a slot length in the housing configured to accommodate the proximal length of the sheath in the second position.

In such embodiments, a distal portion of the sheath can be tapered proximate to the working length of the core wire.

In such embodiments, the catheter assembly can further include a telescopic system including two or more nested telescopic members. At least one telescopic member of the two or more telescopic members can be the sheath.

While some particular embodiments have been provided herein, and while the particular embodiments have been provided in some detail, it is not the intention for the particular embodiments to limit the scope of the concepts presented herein. Additional adaptations and/or modifications can appear to those of ordinary skill in the art, and, in broader aspects, these adaptations and/or modifications are encompassed as well. Accordingly, departures may be made from the particular embodiments provided herein without departing from the scope of the concepts provided herein.

What is claimed is:

1. A method for using an endoluminal device to modify an intravascular lesion, comprising:
    providing an ultrasound-producing mechanism that converts an electric current into vibrational energy at an ultrasonic frequency;
    providing a sheath comprising a first telescoping member and a second telescoping member, the first telescoping member and the second telescoping member defining a sheath lumen, wherein the first telescoping member and the second telescoping member are configured to retract from a first, fully extended position of the sheath, wherein a distal end of the second telescoping member is fully positioned within the first telescoping member and extend from a second, fully retracted position of the sheath, wherein the distal end of the second telescoping member extends distally from the first telescoping member;
    providing a core wire disposed within the sheath lumen of the sheath, the core wire being coupled to the ultrasound-producing mechanism via a sonic connector, the core wire being excited by the vibrational energy at the ultrasonic frequency when the ultrasound-producing mechanism is activated; and
    retracting the first telescoping member and the second telescoping member relative to the core wire to expose a working length of a distal portion of the core wire for ultrasound-based modification of one or more intravascular lesions.

2. The method of claim 1, wherein the act of ultrasound-based modification of one or more intravascular lesions includes at least one of crossing an intravascular lesion and ablating the intravascular lesion.

3. The method of claim 1, wherein the distal portion of the core wire having the working length is wholly disposed within the sheath lumen while the sheath is in the first position.

4. The method of claim 1, wherein a maximum working length of the working length of the distal portion of the core wire is defined by a retraction distance over which a point on the sheath retracts from the first position to the second position.

5. The method of claim 4, wherein the retraction distance is defined by a slot length in a housing that accommodates a proximal length of the sheath when the sheath is in the second position.

6. The method of claim 1, wherein a distal portion of the sheath is tapered.

7. The method of claim 1, comprising vibrating the core wire at a frequency in the range of 20.5 kHz±500 Hz.

8. A method for using an endoluminal device to modify an intravascular lesion, comprising:
    providing a console that includes an ultrasonic generator to convert an alternating electric current into a high-frequency current, an ultrasonic transducer to convert the high-frequency current into a vibrational energy, and an ultrasonic horn to augment an amplitude of the vibrational energy;
    providing a sheath comprising a first telescoping member and a second telescoping member, the first telescoping member and the second telescoping member defining a sheath lumen, wherein the first telescoping member and the second telescoping member are configured to retract from a first, fully extended position of the sheath, wherein a distal end of the second telescoping member is fully positioned within the first telescoping member, and extend from a second, fully retracted position of the sheath, wherein the distal end of the second telescoping member extends distally from the first telescoping member;
    providing a core wire disposed within the sheath lumen of the sheath, the core wire being coupled to the ultrasonic horn via a sonic connector, the core wire being excited by the vibrational energy at the ultrasonic frequency when the ultrasonic generator is activated; and
    retracting the first telescoping member and the second telescoping member relative to the core wire to expose a working length of a distal portion of the core wire for ultrasound-based modification of one or more intravascular lesions.

9. The method of claim 8, wherein the act of ultrasound-based modification of one or more intravascular lesions includes at least one of crossing an intravascular lesion and ablating the intravascular lesion.

10. The method of claim 8, wherein the distal portion of the core wire having the working length is wholly disposed within the sheath lumen while the sheath is in the first position.

11. The method of claim 8, wherein a maximum working length of the working length of the distal portion of the core wire is defined by a retraction distance over which a point on the sheath retracts from the first position to the second position.

12. The method of claim 11, wherein the retraction distance is defined by a slot length in a housing that accommodates a proximal length of the sheath when the sheath is in the second position.

13. The method of claim 8, wherein a distal portion of the sheath is tapered.

14. The method of claim 8, comprising vibrating the core wire at a frequency in the range of 20.5 kHz±500 Hz.

* * * * *

UNITED STATES PATENT AND TRADEMARK OFFICE
CERTIFICATE OF CORRECTION

PATENT NO. : 11,633,206 B2
APPLICATION NO. : 16/462260
DATED : April 25, 2023
INVENTOR(S) : Deepa Deepa It is certified that error appears in the above-identified patent and that said Letters Patent is hereby corrected as shown below:

On the Title Page

In page 4, Column 1, item (56), U.S. patent documents, cite no. 17, delete "6,768,433" and insert --8,768,433--, therefor.

In page 4, Column 1, item (56), U.S. patent documents, cite no. 17, delete "Toth et al." and insert --Jenkins et al.--, therefor.

In page 5, Column 1, item (56), foreign patent documents, cite no. 4, delete "1042435" and insert --4042435--, therefor.

In page 5, Column 2, item (56), foreign patent documents, cite no. 49, delete "9053341" and insert --0053341--, therefor.

In page 5, Column 2, item (56), foreign patent documents, cite no. 50, delete "9067830" and insert --0067830--, therefor.

In page 5, Column 2, item (56), foreign patent documents, cite no. 52, delete "93039381" and insert --03039381--, therefor.

Signed and Sealed this
Twenty-seventh Day of June, 2023

Katherine Kelly Vidal
*Director of the United States Patent and Trademark Office*